US009541614B2

(12) United States Patent
Soutome et al.

(10) Patent No.: US 9,541,614 B2
(45) Date of Patent: Jan. 10, 2017

(54) HIGH FREQUENCY COIL UNIT AND MAGNETIC RESONANCE IMAGING APPARATUS

(75) Inventors: Yoshihisa Soutome, Tokyo (JP); Yoshitaka Bito, Tokyo (JP); Hideta Habara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 650 days.

(21) Appl. No.: 14/001,221

(22) PCT Filed: Apr. 6, 2012

(86) PCT No.: PCT/JP2012/059574
§ 371 (c)(1),
(2), (4) Date: Dec. 5, 2013

(87) PCT Pub. No.: WO2012/141106
PCT Pub. Date: Oct. 18, 2012

(65) Prior Publication Data
US 2014/0103931 A1 Apr. 17, 2014

(30) Foreign Application Priority Data
Apr. 11, 2011 (JP) .................................. 2011-087146

(51) Int. Cl.
*G01R 33/34* (2006.01)
*A61B 5/055* (2006.01)

(52) U.S. Cl.
CPC ............... *G01R 33/34* (2013.01); *A61B 5/055* (2013.01); *G01R 33/34076* (2013.01)

(58) Field of Classification Search
CPC .................. G01R 33/34046; G01R 33/34076; G01R 33/34; A61B 5/055
See application file for complete search history.

(56) References Cited

U.S. PATENT DOCUMENTS 4,686,473 A * 8/1987 Chesneau ........ G01R 33/34076
324/319
4,737,718 A 4/1988 Kemner et al.
(Continued)

FOREIGN PATENT DOCUMENTS

JP  62-44239 A  2/1987
JP  6244239 A  2/1987
(Continued)

OTHER PUBLICATIONS

S. Li et al.: "A Method to Create an Optimum Current Distribution and Homogeneous B1 Field for Elliptical Birdcage Coils", Magnetic Resonance in Medicine, 1997.04, vol. 37, No. 4, pp. 600-608.
(Continued)

*Primary Examiner* — Clayton E Laballe
*Assistant Examiner* — Ruifeng Pu
(74) *Attorney, Agent, or Firm* — Brundidge & Stanger, P.C.

(57) ABSTRACT

The present invention is directed to an elliptical birdcage coil which reduces time and effort upon manufacturing and production cost, with less variations in performance. There is provided a high frequency coil unit made up of the elliptical birdcage coil having plural capacitors arranged at least on either of the ring conductors and the rung conductors, the capacitance of the plural capacitors being uniform with respect to each conductor type on which the capacitors are placed. In this elliptical birdcage coil, a value of inductance and arrangement of the ring conductors and the rung conductors are determined in such a manner that the capacitance of the capacitors becomes identical with respect to each conductor type on which the capacitors are arranged.

18 Claims, 17 Drawing Sheets

(56) References Cited

U.S. PATENT DOCUMENTS

| | | | |
|---|---|---|---|
| 4,916,418 A | | 4/1990 | Rath |
| 5,986,454 A | | 11/1999 | Leifer |
| 6,043,658 A | * | 3/2000 | Leussler .......... G01R 33/34046 324/309 |
| 2008/0061785 A1 | * | 3/2008 | Soutome .......... G01R 33/34076 324/319 |
| 2010/0253333 A1 | * | 10/2010 | Zhai ................. G01R 33/34046 324/307 |
| 2011/0018539 A1 | * | 1/2011 | Viswanathan ......... B82Y 10/00 324/318 |
| 2012/0262173 A1 | * | 10/2012 | Soutome .......... G01R 33/34076 324/309 |
| 2014/0145722 A1 | * | 5/2014 | Suzuki ............... G01R 33/3628 324/322 |

FOREIGN PATENT DOCUMENTS

| | | |
|---|---|---|
| JP | 03-131235 | 6/1991 |
| JP | 3095402 B2 | 10/2000 |

OTHER PUBLICATIONS

N. De Zanche et al.: "Sensitivity Calculations and Comparisons for Shielded Elliptical and Circular Birdcage Coils", Magnetic Resonance in Medicine, 2002.02, vol. 47, No. 2, pp. 364-371.

International Preliminary Report on Patentability issued in corresponding application No. PCT/JP2012/059574 on Oct. 15, 2013.

J. Tropp: "The Theory of the Bird-Cage Resonator", Journal of Magnetic Resonance,(1989) vol. 82, pp. 51-62.

J. T. Vaughan et al.: "High Frequency Volume Coils for Clinical NMR Imaging and Spectroscopy", Magnetic Resonance in Medicine, (1994) vol. 32, pp. 206-218.

C. N. Chen et al.: "Quadrature Detection Coils—A Further $\sqrt{2}$ Improvement in Sensitivity", Journal of Magnetic Resonance, (1983) vol. 54, pp. 324-327.

M. C. Leifer: "Theory of the Quadrature Elliptic Birdcage Coil", Magnetic Resonance in Medicine, 1997.11, vol. 38, No. 5, pp. 726-732.

International Search Report issued in corresponding application No. PCT/JP2012/059574 on May 22, 2012.

* cited by examiner

HIGH FREQUENCY COIL UNIT AND MAGNETIC RESONANCE IMAGING APPARATUS

TECHNICAL FIELD

The present invention relates to a magnetic resonance imaging (MRI) technique, and more particularly, it relates to a technique for carrying out irradiation of electromagnetic waves and detection of magnetic resonance signals.

BACKGROUND ART

An MRI (magnetic resonance imaging) apparatus is a medical diagnostic imaging apparatus that produces magnetic resonance in a nuclear spin within an arbitrary cross section passing transversely across a test subject, and obtains a tomographic image in the cross section based on the magnetic resonance signals being generated. When a test subject placed in a static magnetic field is irradiated with an RF magnetic field from a high frequency coil (RF coil), together with application of a gradient magnetic field, a nuclear spin within the test subject, a nuclear spin of hydrogen atom, for instance, is excited. When the nuclear spin being thus excited restores to an equilibrium state, a magnetic field of circularly polarized wave occurs as a magnetic resonance signal. The RF coil detects this signal, and the signal is subjected to a signal processing so as to create an image representing a distribution of atomic nuclei of hydrogen within a living body.

There are some types for this RF coil, including a transmission coil exclusively used for irradiation of the RF magnetic field, a reception coil exclusively used for receiving the magnetic resonance signal, and a transceive coil used for both transmission and reception. Various kinds of coils are developed for each of those types, in order to efficiently obtain an image of high quality. For example, when the nuclear spin within the test subject is excited, it is necessary to have a homogeneous distribution of the RF magnetic field. It is desirable that a degree of the homogeneity is within 70% with respect to a maximum value of the distribution of the RF magnetic field in the imaging region. This is because if high inhomogeneity exists in the distribution of the RF magnetic field, a difference may occur in the excited state of the nuclear spins, depending on portions in the test subject, and unevenness of contrast and/or an artifact may be generated in the image being obtained. As the RF coil having this kind of homogeneous distribution of irradiation strength, there are known cylindrical RF coils such as a birdcage coil (e.g., see Patent Document 1 and Non Patent Document 1), and TEM coil (e.g., see Non Patent Document 2). The birdcage coil is made up of two cylindrical ring conductors, plural linear rung conductors, and plural capacitors. Here, the ends of the rung conductors are connected to the ring conductors, and the capacitors are placed on the ring conductors or on the rung conductors.

Furthermore, it is necessary to enhance the irradiation efficiency. As a method for enhancing the irradiation efficiency, there is a method of quadrature phase detection (QD: Quadrature Detection) (see Patent Document 2 and Non Patent Document 3, for instance). The QD method uses two RF coils for irradiation of high frequency magnetic fields being orthogonal to each other, and irradiation of the RF magnetic fields is performed in such a manner that a phase difference in time phase is 90 degrees between the respective irradiation of the RF magnetic fields from the RF coils. The QD method allows the circularly polarized wave field for exciting the nuclear spin of the hydrogen atom to be irradiated with a high degree of efficiency, and therefore, the irradiation strength can be enhanced theoretically by $\sqrt{2}$, compared to the case of irradiation by one RF coil. If it is converted into irradiation power, only a half of the power is required, and therefore the irradiation efficiency is doubled. When the birdcage coil or the TEM coil is employed, two feeding ports used for the irradiation are arranged at the positions orthogonal to each other, thereby enabling irradiation of the RF magnetic fields according to the QD method, just by one coil.

Since the trunk of the test subject has a shape similar to an elliptic cylindrical shape, an elliptic cylindrical shape rather than a cylindrical shape enables enhancement of a ratio which represents occupancy of the test subject within the coil (filling factor), thereby improving the irradiation efficiency of the RF coil. Accordingly, an elliptical birdcage coil having an elliptic cylindrical shape is developed (see Patent Document 3, Non Patent Document 4, and Non Patent Document 5, for instance).

PRIOR ART DOCUMENT

Patent Document

Patent Document 1: U.S. Pat. No. 4,916,418 Specification
Patent Document 2: Japanese Patent No. 3095402
Patent Document 3: U.S. Pat. No. 5,986,454 Specification

Non Patent Document

Non Patent Document 1: J. Tropp, "The Theory of the Bird-Cage Resonator", Journal of Magnetic Resonance, (1989) Vol. 82, pp. 51-62
Non Patent Document 2: J. T. Vaughan, et al., "High frequency volume coils for clinical nuclear magnetic resonance imaging and spectroscopy", Magnetic Resonance in Medicine, (1994) Vol. 32, pp. 206-218
Non Patent Document 3: C. N. Chen, et al., "Quadrature Detection Coils—A Further $\sqrt{2}$ Improvement in Sensitivity", Journal of Magnetic Resonance, (1983) Vol. 54, pp. 324-327
Non Patent Document 4: M. C. Leifer, "Theory of the Quadrature Elliptic Birdcage Coil", Magnetic Resonance in Medicine, (1997) Vol. 38, pp. 726-732
Non Patent Document 5: S. Li, et al., "A Method to Create an Optimum Current Distribution and Homogeneous B1 Field for Elliptical Birdcage Coils", Magnetic Resonance in Medicine, (1997) Vol. 37, pp. 600-608

DISCLOSURE OF THE INVENTION

Problem to be Solved by the Invention

Unlike a cylindrical birdcage coil, capacitance of capacitors arranged on ring conductors or rung conductors of an elliptical birdcage coil is different depending on the place where the capacitor is placed, since distance between conductors is various. Therefore, upon manufacturing the coil, it is necessary to prepare capacitors with various capacitance depending on locations for installation. The capacitance of a typically available capacitor is limited to a predetermined value, and in order to obtain desired capacitance, it is required to combine plural capacitors in series or in parallel. Therefore, various combinations of capacitors are prepared, being different depending on the locations for installation, upon manufacturing the coil. This is time-consuming, and there is a drastic increase in the number of variations as to the capacitance of capacitors being used, causing a rise in manufacturing cost. In addition, a difference in capacitance of plural capacitors being combined changes the Q-value of the capacitors. Therefore, variations in high-frequency property may occur depending on the locations for installation, and this may increase variations in coil performance.

The present invention has been made in view of the situation above, and an object of the present invention is to obtain an elliptical birdcage coil which reduces time and effort upon manufacturing and production cost, with less variations in performance.

Means to Solve the Problem

The present invention provides an RF coil unit made up of an elliptical birdcage coil with plural capacitors arranged on at least either of a ring conductor and a rung conductor, and capacitance of the capacitors is uniform with respect to each type of the conductors on which the capacitors are placed. In this elliptical birdcage coil, a value of inductance and arrangement of the ring conductors and the rung conductors are determined in such a manner that the capacitance of the capacitors becomes identical for each type of the conductors on which the capacitors are arranged.

Specifically, an RF coil is provided, including, plural linear conductors arranged along an elliptic cylindrical curved surface in parallel with the central axis thereof, two elliptical loop conductors that are arranged, setting a point on the central axis as a center, in such a manner that loop surfaces are parallel with each other along the elliptic cylindrical curved surface, and plural first capacitors, each made up of at least one capacitor, both ends of each of the linear conductors being connected to the elliptical loop conductors, respectively, the first capacitors being arranged one by one respectively on either of the linear conductors and arcuate conductors of the elliptical loop conductor, the arcuate conductor being placed between connection points with the linear conductors being adjacent, the plural linear conductors being arranged at positions line-symmetrical with respect to the major axis and the minor axis of the elliptical loop conductor, and the capacitance of the first capacitors being an identical value.

In addition, there is provided a magnetic resonance imaging apparatus being provided with; a static magnetic field generator for generating a static magnetic field, a gradient magnetic field applying device for applying a gradient magnetic field, an RF magnetic field signal generator for generating an RF magnetic field signal, a transceive coil for irradiating a test subject with the RF magnetic field signal inputted from the RF magnetic field signal generator, detecting a magnetic resonance signal issued from the test subject, and outputting the signal as a detection signal, a signal processor for subjecting the detection signal to a signal processing, and a controller for controlling operations of the gradient magnetic field applying device, the RF magnetic field signal generator, and the signal processor; wherein, the aforementioned RF coil unit is employed as the transceive coil.

Effect of the Invention

According to the present invention, it is possible to easily obtain an elliptical birdcage coil being low in cost and less variations in performance. This allows reduction of trouble and effort upon manufacturing, production cost, and variations in coil performance of the elliptical birdcage coil.

BEST MODE FOR CARRYING OUT THE INVENTION

First Embodiment

Hereinafter, the first embodiment to which the present invention is applied will be explained. In all the following figures for explaining the embodiments of the present invention, the constituents having the same function are labeled the same, and tedious explanations will not be made.

Figure 1:
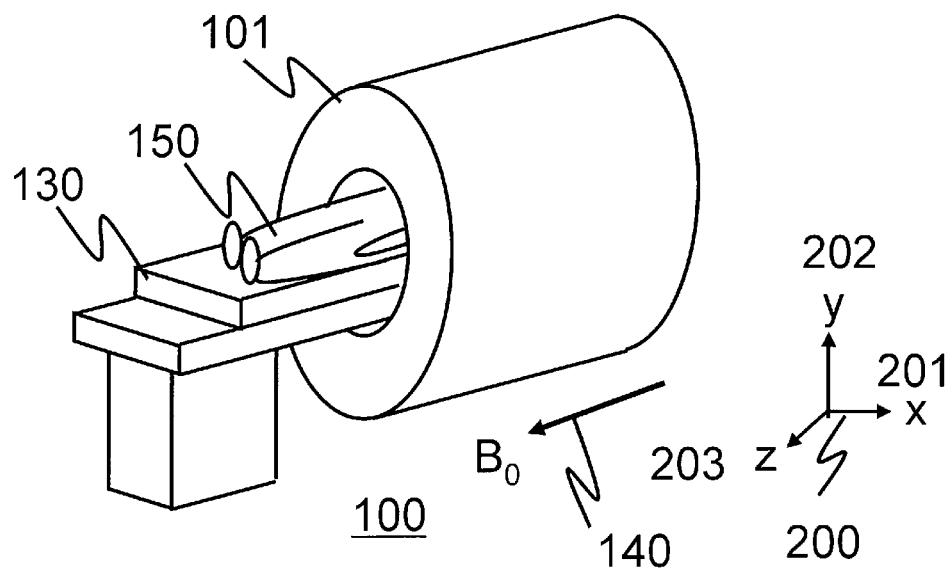
FIG. 1 illustrates an overview of an MRI apparatus according to the first embodiment.

Firstly, an overall configuration of the MRI apparatus according to the present embodiment will be explained. FIG. 1 illustrates an overview of the MRI apparatus according to the present embodiment. FIG. 1 illustrates the MRI apparatus 100 provided with a magnet 101 intended for a horizontal magnetic field system. The test subject 150 is inserted into the imaging space within a bore of the magnet 101 in the state of being laid on a table 130, and subjected to imaging. It is to be noted that the present embodiment employs the coordinate system 200 in which the static magnetic field 140 ($B_0$) generated by the magnet 101 of the horizontal magnetic field system is in the direction of z-axis 203.

Figure 2:
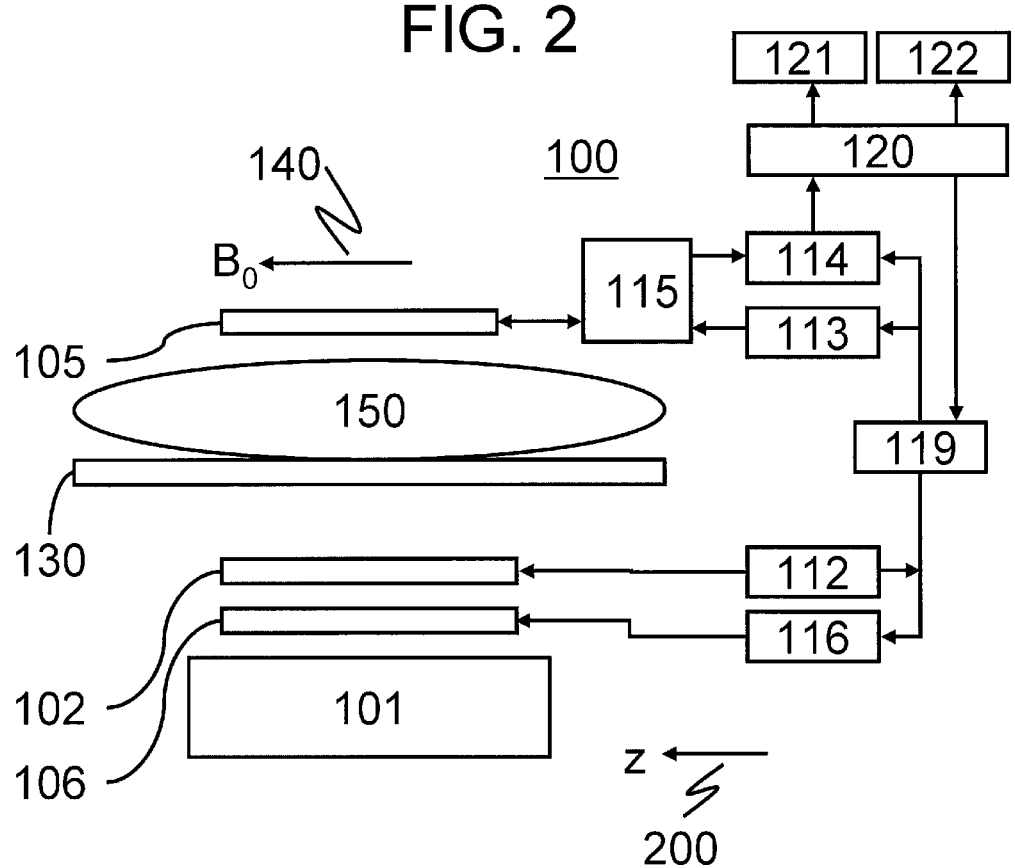
FIG. 2 is a block diagram showing a schematic configuration of the MRI apparatus according to the first embodiment.

FIG. 2 is a block diagram showing a schematic configuration of the MRI apparatus 100 according to the present embodiment. The same constituents as those in FIG. 1 are labeled the same. The MRI apparatus 100 according to the present embodiment is provided with the magnet 101 of the horizontal magnetic field system (static magnetic field generator), a gradient magnetic field coil 102, a shim coil 106 for adjusting homogeneity of the static magnetic field, a sequencer 119, a transceive RF coil 105 for generating an RF magnetic field and receiving a magnetic resonance signal (transmit-receive coil), a transmit/receive switching unit 115, a power supply for gradient magnetic field 112, an RF magnetic field generator 113 (RF magnetic field signal generator), a receiver 114, a power supply for shim coil 116, a storage medium 122, a computer 120 (controller), a display unit 121, and the table 130.

The gradient magnetic field coil 102 and the shim coil 106 are connected respectively to the power supply for gradient magnetic field 112 and the power supply for shim coil 116. The transceive RF coil 105 is connected to the RF magnetic field generator 113 and the receiver 114 via the transmit/receive switching unit 115. The sequencer 119 sends a command to each of the power supply for gradient magnetic field 112, the power supply for shim coil 116, and the RF magnetic field generator 113, thereby generating a gradient magnetic field and an RF magnetic field, respectively. The RF magnetic field is applied to the test subject 150 via the transceive RF coil 105. By applying the RF magnetic field, the transceive RF coil 105 detects a magnetic resonance signal generated from the test subject 150, and the receiver 114 performs wave detection. The sequencer 119 sets a magnetic resonance frequency that is assumed as a reference for the wave detection in the receiver 114. The signal subjected to the wave detection is transferred to the computer 120 via the A/D converter, and in here, signal processing such as image reconstruction is performed on the signal. The display unit 121 displays the result. The storage medium 122 stores the signal after the wave detection and measuring conditions, as appropriate. The sequencer 119 carries out control in such a manner that each unit is operated at a timing and with strength being programmed in advance.

Next, an explanation will be made as to the RF coil unit 310 that is used as the transceive RF coil 105 in the MRI apparatus 100 according to the present embodiment. The RF coil unit 310 of the present embodiment is an elliptical birdcage coil that enables homogeneous distribution of irradiation within the test subject 150 and also irradiation according to the QD method.

Figure 3A:
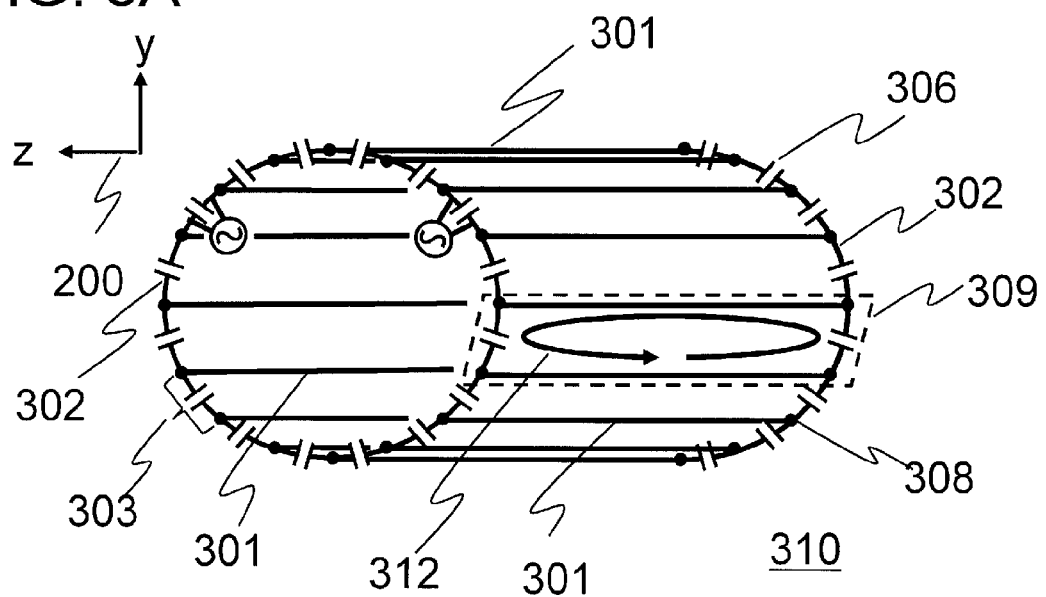
FIG. 3A illustrates the RF coil unit according to the first embodiment.
Figure 3B:
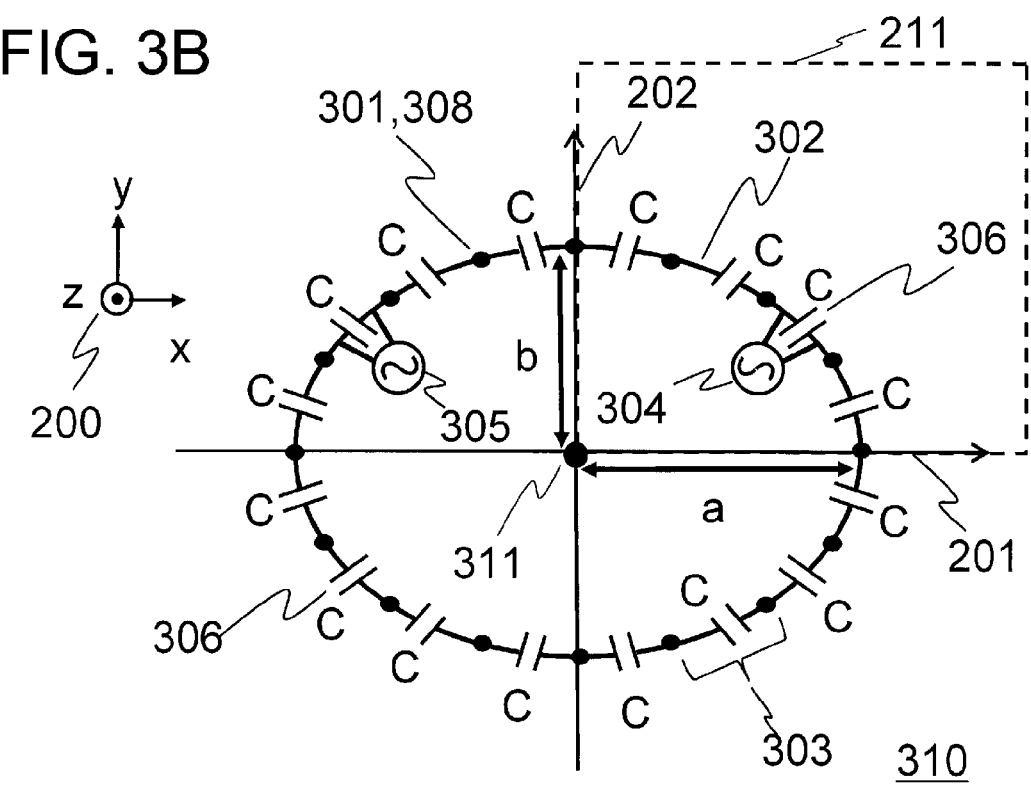
FIG. 3B illustrates the RF coil unit according to the first embodiment.
Figure 4A:
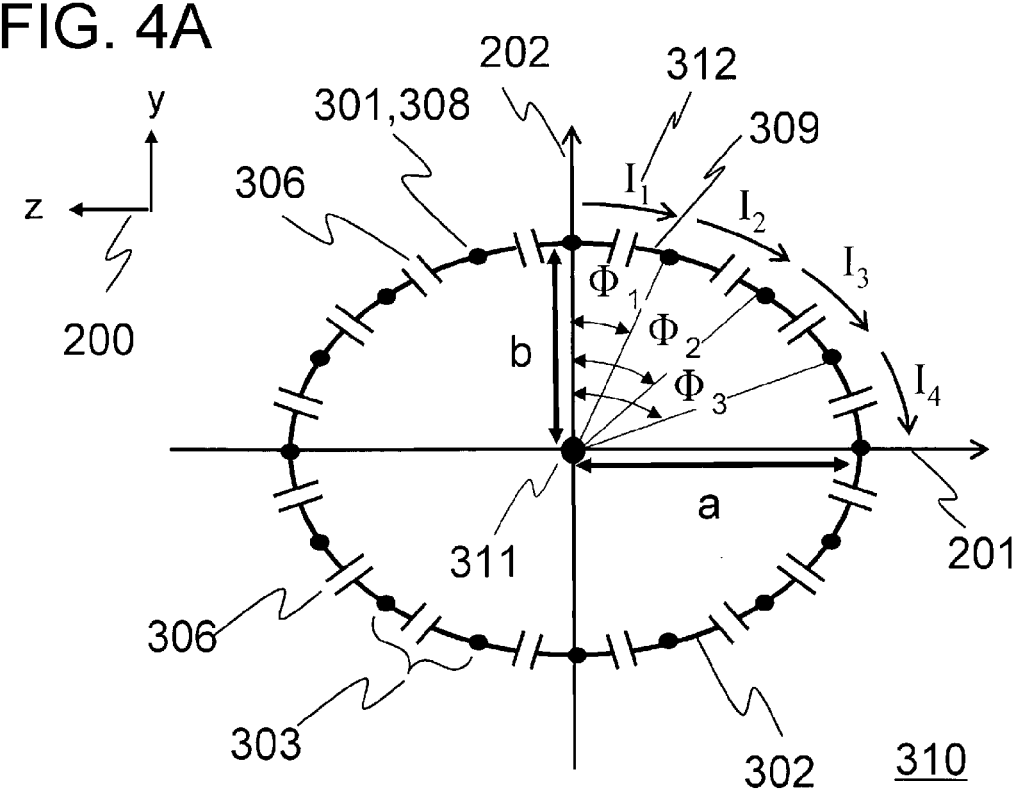
FIG. 4A illustrates the RF coil unit according to the first embodiment.
Figure 4B:
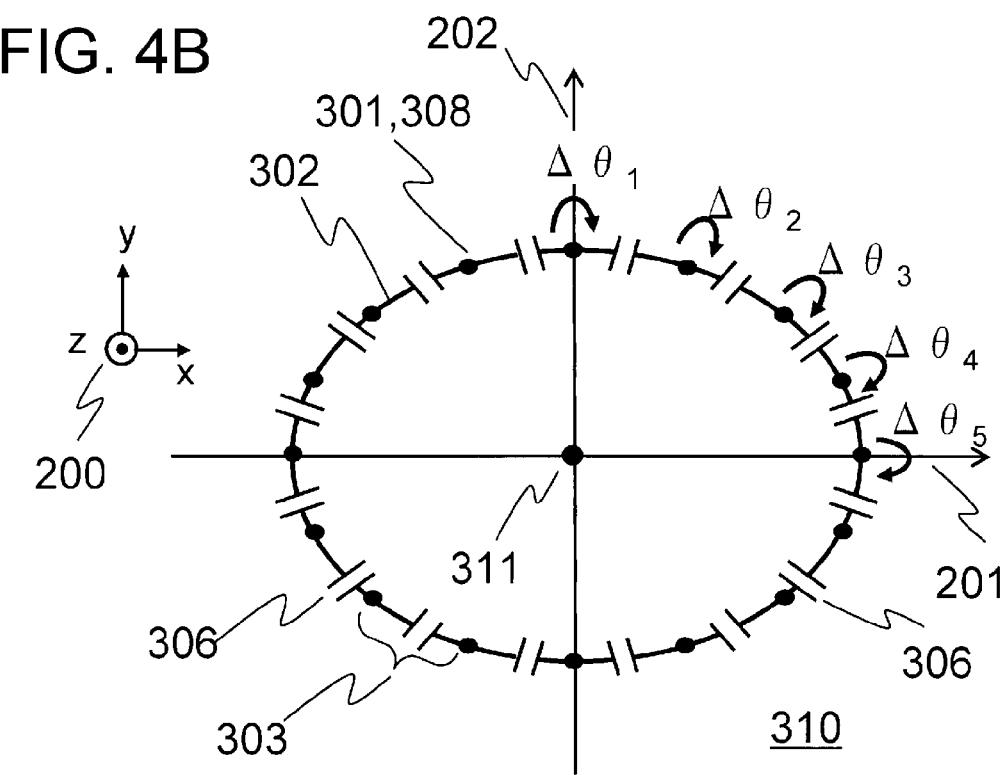
FIG. 4B illustrates the RF coil unit according to the first embodiment.

FIG. 3A, FIG. 3B FIG. 4A and FIG. 4B illustrate a configuration of the RF coil unit 310 according to the present embodiment. FIG. 3A is an illustration viewing the RF coil unit 310 obliquely, and FIG. 3B, FIG. 4A, and FIG. 4B are illustrations of the RF coil unit 310 viewed in the direction of the central axis 311.

As shown in FIG. 3A, FIG. 3B, and FIG. 4A, the RF coil unit 310 is provided with 4N linear conductors 301 (N is a natural number; N=4 in the figure) along an elliptic cylindrical curved surface, arranged in parallel with the central axis 311 of the elliptic cylindrical curved surface having a major axis diameter $2a$ and a minor axis diameter $2b$, two elliptical loop conductors 302 arranged along the elliptic cylindrical curved surface setting as a center a point on the central axis 311, 8N first capacitors 306 (in the figure, N=4), a first feeding port 304, and a second feeding port 305.

The RF coil unit 310 of the present embodiment is arranged in such a manner that the direction of the central axis 311 is assumed as the direction of the z-axis of the coordinate system 200, the major axis direction of the ellipse formed by the elliptical loop conductor 302 is assumed as the direction of the x-axis 201, and the minor axis direction is assumed as the direction of the y-axis 202.

The two elliptical loop conductors 302 are arranged so that loop surfaces of the respective conductors are parallel with each other. In the ellipse formed by the elliptical loop conductor 302, the major axis diameter is assumed as $2a$, and the minor axis diameter is assumed as $2b$, similar to the elliptic cylindrical curved surface. Hereinafter, in the present specification, the major axis, the minor axis, and the center of the ellipse formed by the elliptical loop conductor 302 are referred to as the major axis, the minor axis, and the center of the elliptical loop conductor 302, respectively.

As shown in FIG. 3A, both ends of the 4N linear conductors 301 are respectively connected to the elliptical loop conductors 302, via the connection points 308. On the elliptical loop conductor 302, a conductor portion having adjacent two connection points at both ends is referred to as an arcuate conductor 303. On this occasion, adjacent two linear conductors 301, and two arcuate conductors 303 between both the linear conductors 301 form a loop 309.

The 4N linear conductors 301 arranged in such a manner that they are line symmetrical with respect to the x-axis 201 and the y-axis 202. In the present embodiment, as shown in FIG. 3B, four line conductors 301 out of the 4N linear conductors 301, are arranged in such a manner that they pass through any of the crossing points between the elliptical loop conductor 302 and the x-axis 201, and the crossing points between the elliptical loop conductor 302 and the y-axis 202, respectively, and remaining 4(N−1) linear conductors 301 are arranged at the positions line-symmetrical with respect to the major axis and the minor axis of the elliptical loop conductor 302. The linear conductor 301 and the elliptical loop conductor 302 will be described in detail later.

Both the first feeding port 304 and the second feeding port 305 are arranged respectively, at the positions line-symmetrical with respect to the y-axis 202 or the x-axis 201, and when power is fed to one feeding port, those positions minimize the amplitude of the RF current flowing in the other feeding port. By way of example, those feeding ports are connected respectively to first capacitors 306 being in line-symmetrical relationship with respect to the y-axis 202 or the x-axis 201, and an electrical phase difference therebetween falls into the range from 75 to 105 degrees. It is found by simulation that when power is fed to one feed port, the amplitude of the RF current flowing in the other feeding port is minimized in the case where the electrical phase difference between the two feeding ports falls into the range from 75 to 105 degrees. Hereinafter, an example will be explained, as to the case where the feeding ports are connected respectively with two first capacitors 306, in the line symmetrical relationship with respect to the y-axis 202, and the electrical phase difference therebetween falls into the range from 75 to 105 degrees.

The first feeding port 304 and the second feeding port 305 are connected to a QD hybrid (not illustrated) respectively via coaxial cables. An output from the QD hybrid is connected to the transmit/receive switching unit 115. It is to be noted that the QD hybrid is a two-input and two-output circuit, and when the input signal is one, this signal is distributed into two signals with signal waveforms having a phase difference of 90 degrees, and those signals are outputted. If there are two input signals, the phase of one signal is shifted by 90 degrees, thereby combining those signals and outputs the signal thus combined.

The first capacitors 306 are placed one by one respectively on the arcuate conductors 303. In the present embodiment, the capacitance of each of the first capacitors 306 is identical with one another. The capacitance is adjusted in such a manner that the RF coil unit 310 becomes the resonant state at the magnetic resonance frequency ($f_c$) used in the transceive RF coil 105. It is to be noted that the first capacitor 306 may be made up of plural capacitors. In the case where the first capacitor 306 is made up of plural capacitors, the combined capacitance of those capacitors is assumed as the capacitance of the first capacitor 306.

Next, an explanation will be made as to a configuration of the linear conductor 301 and the elliptical loop conductor 302, so as to establish the RF coil unit 310 as an elliptical birdcage coil, setting each of the first capacitors 306 to have an identical capacitance, having an irradiation distribution that is homogeneous within the test subject 150, and implementing irradiation by the QD method, further achieving an elliptical birdcage coil in which resonance occurs at the magnetic resonance frequency ($f_c$) used in the transceive RF coil 105.

Arrangement of the (N−1) linear conductors 301 in each quadrant of the coordinate plane defined by the x-axis 201 and the y-axis 202 will be explained, taking as an example that N−1 (three in the figure) of linear conductors 301 are arranged in the first quadrant 211. As for the N−1 linear conductors 301 placed in the first quadrant 211, the connection points 308 are arranged, as shown in FIG. 4A, in such a manner that the angle $\phi_m$ (m=1, 2, . . . , N−1) formed by the connection points with the y-axis 202 satisfies the following formula (1):

[Formula 1]

$$\Phi_m = \tan^{-1}\left(\frac{b}{a}\tan\left(\sum_{k=1}^{m}\frac{\Delta\theta_k + \Delta\theta_{k+1}}{2}\right)\right) \quad (1)$$

Here, $\Delta\theta_k$ represents an electrical phase difference ($\Delta\theta_k=\theta_k-\theta_{k-1}$) being a difference between the phase $\theta_k$ of the loop current $I_k$ 312 flowing in the k-th loop 309 (1≤k≤N−1) counted starting from near the y-axis 202 in the first quadrant 211, and the phase $\theta_{k-1}$ of the loop current $I_{k-1}$ 312 flowing in the (k−1)th loop 309. It is to be noted that $\theta_0$ is assumed as the phase of the loop current 312 flowing in the loop 309 being the closest to the y-axis in the second quadrant, and $\theta_N$ is assumed as the phase of the loop current 312 flowing the loop 309 being the closest to the x-axis 201 in the fourth quadrant. By way of example, if the loop 309 being the closest to the y-axis 202 in the first quadrant 211 is assumed as the first loop, and numbers are assigned to the loops 309 in clockwise, $\theta_0$ represents the phase of the loop current 312 of the 4N-th loop 309, and $\theta_N$ represents the phase of the loop current 312 of the N-th loop 309.

As described above, the connection points 308 of the 4N linear conductors 301 are arranged on the elliptical loop conductor 302 at point-symmetrical positions, setting the center of the elliptical loop conductor 302 as the point of symmetry. Therefore, N−1 (three in the figure) linear conductors 301 in the second quadrant are arranged at the positions line-symmetrical with N−1 (three in the figure) linear conductors 301 in the first quadrant, with respect to y-axis 202, the three linear conductors 301 in the third quadrant are arranged at the positions line-symmetrical with the N−1 (three in the figure) linear conductors 301 in the second quadrant with respect to the x-axis 201, and N−1 (three in the figure) linear conductors 301 in the fourth quadrant are arranged at the positions line-symmetrical with the three linear conductors 301 in the first quadrant with respect to the x-axis 201.

In the RF coil unit 310, the electrical phase difference $\Delta\theta_k$ between the adjacent arcuate conductors 303 is adjusted so that the following formula (2), formula (3), formula (4), formula (5), and formula (6) are satisfied:

$$\Delta\theta_k > 0 \quad (2)$$

$$\Delta\theta_{k-1} < \Delta\theta_k (1 < k < N+1) \quad (3)$$

[Formula 4]

$$\sum_{k=1}^{N}\frac{\Delta\theta_k + \Delta\theta_{k+1}}{2} = \frac{\pi}{2} \quad (4)$$

[Formula 5]

$$\sin(\Delta\theta_{k+1}) = \frac{L_k^l}{L_{k+1}^l}\sin(\Delta\theta_k) \quad (5)$$

[Formula 6]

$$\cos(\Delta\theta_{k'+1}) = 1 + \frac{1}{L_{k'+1}^l}((L_{k'}^r - L_{k'-1}^r) + L_{k'-1}^l(\cos(\Delta\theta_{k'-1}) - 1)) \quad (6)$$

Here, k is an integer satisfying N+1>k>0, and k' is an integer satisfying N>k'>0. In addition, $L_m^r$ (m=1, 2, . . . , N) represents an equivalent inductance of the m-th arcuate conductor 303 counting in clockwise, in the circumferential direction of the elliptical loop conductor 302 from the y-axis 202 in the first quadrant 211 in FIG. 3B, and $L^l_m$ (m=1, 2, ..., N+1) represents an equivalent inductance of the m-th linear conductor 303 counting in clockwise, in the circumferential direction of the elliptical loop conductor 302 from the y-axis 202. The equivalent inductance of the linear conductor 301 having the connection point on the y-axis 202 is represented by $L^l_0$.

Figure 5:
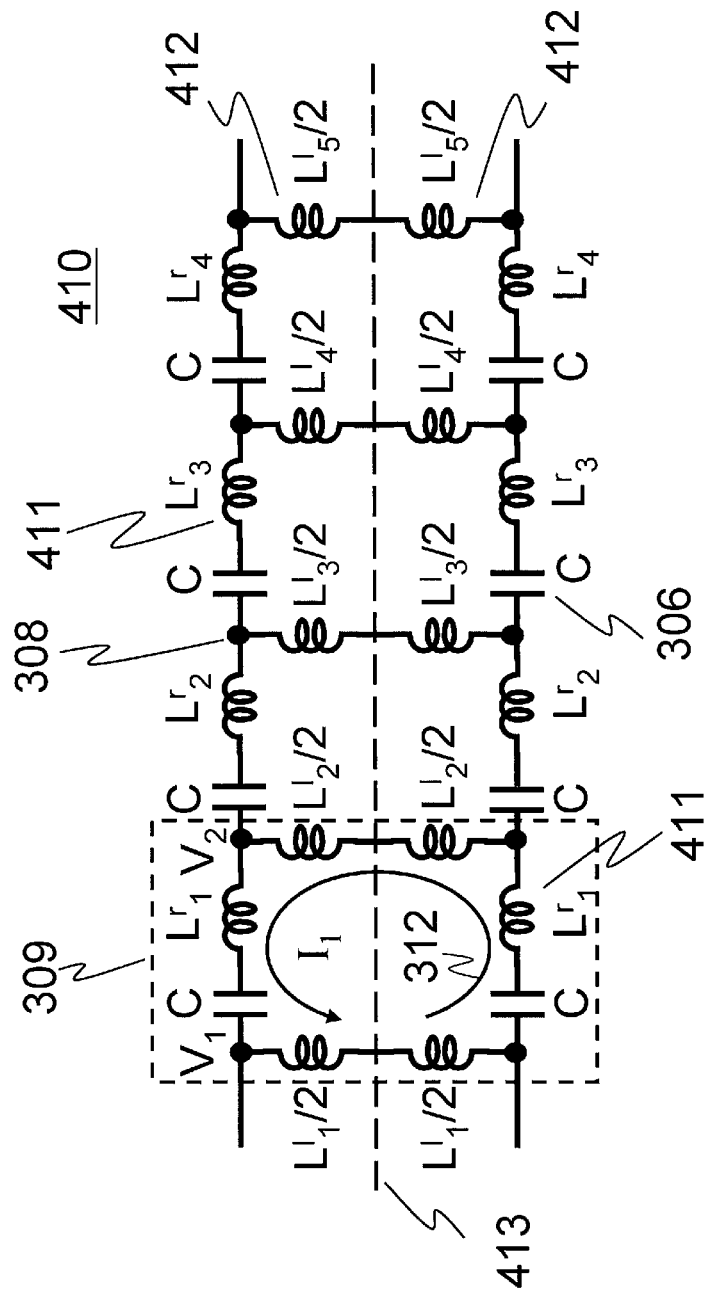
FIG. 5 is a circuit diagram illustrating a partial equivalent circuit of the RF coil according to the first embodiment.

The formula (5) and the formula (6) are derived from the equivalent circuit 410 in the part of the first quadrant 211 in the RF coil unit 310 as shown in FIG. 3B. FIG. 5 illustrates the equivalent circuit 410. The equivalent circuit 410 is obtained by developing the part of the first quadrant 211 of the RF coil unit 310 in a plane. A value of the first capacitor 306 is represented by C. In addition, the inductance of the arcuate conductor 303 is indicated by the reference number 411, and the inductance of the linear conductor 301 is indicated by the reference number 412. Here, since the equivalent circuit 410 is symmetrical with respect to the vertical direction of FIG. 5 on paper, a virtual ground 413 is set at the middle point of the linear conductor 301.

On this occasion, voltage $V_k$ between the connection point 308 of the k-th linear conductor 301 counting in clockwise in the circumferential direction of the elliptical loop conductor 302 from the y-axis 202, and the virtual ground 413 is represented by the formula (7) according to the Kirchhoff's circuit laws:

[Formula 7]

$$V_k = j\omega L^l_k (I_k - I_{k-1})/2 \tag{7}$$

Here, $I_k$ represents the loop current 312 flowing in the k-th loop 309 counted starting from near the y-axis 202 in the first quadrant 211.

In addition, a difference between the voltage $V_{k+1}$ and the voltage $V_k$ is expressed by the formula (8) from the equivalent circuit 410 as shown in FIG. 5:

[Formula 8]

$$V_{k+1} - V_k = \left(j\omega L^r_k + \frac{1}{j\omega C}\right) I_k \tag{8}$$

Here, when the formula (7) is substituted into the formula (8), the formula (9) is obtained:

[Formula 9]

$$\frac{2}{\omega^2 C} = 2L^r_k - L^l_{k+1}\left(\frac{I_{k+1}}{I_k} - 1\right) - L^l_k\left(\frac{I_{k-1}}{I_k} - 1\right) \tag{9}$$

The loop current 312 represented by $I_k$ is expressed by the formula (10):

$$I_k = A \cdot \exp(j(\omega t + \theta_k)) \tag{10}$$

Since $\Delta\theta_k = \theta_k - \theta_{k-1}$, $I_{k+1}/I_k$ and $I_k/I_{k-1}$ being the ratio of the loop current 312 in the adjacent loops 309 are expressed by the formula (11) and the formula (12):

$$I_{k+1}/I_k = \exp(j\Delta\theta_{k+1}) \tag{11}$$

$$I_k/I_{k-1} = \exp(j\Delta\theta_k) \tag{12}$$

If modifications are made using the formulas above, the formula (9) is expressed by the formula (13):

[Formula 13]

$$\frac{2}{\omega^2 C} = 2L^r_k - L^l_{k+1}(\exp(j\Delta\theta_{k+1}) - 1) - L^l_k(\exp(-j\Delta\theta_k) - 1) \tag{13}$$

Here, C represents a value of the first capacitor 306, and it is constant. In addition, ω represents resonant angular frequency of the coil, and it is constant independent of k.

If a solution is obtained as to $\Delta\theta_{k+1}$, by using the formula in which (k−1) is substituted for k in the formula (13) together with the formula (13), the formula (14) is obtained:

[Formula 14]

$$\exp(j\Delta\theta_{k+1}) = 1 + \frac{2(L^r_k - L^r_{k-1}) + j2L^l_k \sin(\Delta\theta_k) + L^l_{k-1}(\exp(-j\Delta\theta_{k-1}) - 1)}{L^l_{k+1}} \tag{14}$$

If the real part of the formula (14) is solved, the formula (6) as described above is obtained. On the other hand, if the imaginary part of the formula (14) is solved, the formula (15) is obtained:

[Formula 15]

$$\sin(\Delta\theta_{k+1}) = \frac{2L^l_k}{L^l_{k+1}}\sin(\Delta\theta_k) - \frac{L^l_{k-1}}{L^l_{k+1}}\sin(\Delta\theta_{k-1}) \tag{15}$$

Here, $L^l_0$ represents the inductance of the linear conductor at the position being the closest to the y-axis 202 in the second quadrant in FIG. 3B, and it becomes equal to $L^l_2$, according to the symmetric property of the shape of the coil. In addition, according to the symmetric property of the shape of the coil, $\Delta\theta_0$ becomes equal to $\Delta\theta_2$. Then, assuming that $L^l_0 = L^l_2$ and $\Delta\theta_0 = \Delta\theta_2$, when the formula (15) is modified for the case of k=1, the formula (5) is obtained for the case of k=1.

In addition, if the formula in which k is replaced by k−1 is substituted into the second term on the right side of the formula (15), the formula (15) becomes equivalent to the formula (5).

In addition, $L^l_{N+2}$ indicates the inductance of the linear conductor 301 being the closest to the x-axis 201 in the fourth quadrant as shown in FIG. 3B, and according to the symmetric property of the coil shape, it becomes equal to $L^l_N$. According to the symmetric property of the coil shape, $\Delta\theta_{N+2}$ also becomes equal to $\Delta\theta_N$. Therefore, assuming that $L^l_{N+2} = L^l_N$ and $\Delta\downarrow_{N+2} = \Delta\theta_N$, when the formula (15) for the case of k=N+1, the formula (5) for the case of k=N+1 is obtained.

Next, an explanation will be made as to a method for calculating the equivalent inductance $L^l_m$ and $L^r_m$ of the linear conductor 301 and the elliptical loop conductor 302 (arcuate conductor 303) that are used in the formula (5) and the formula (6).

The equivalent inductance $L^l_k$ of the linear conductor 301 is obtained, as a sum of the self inductance $L^{ls}_k$ obtained from the shape of the linear conductor 301 and the mutual inductance $M^l_{k,k-1}$, $M^l_{k,k+1}$ of the adjacent linear conductors 301. In other words, it is expressed by the formula (16) (see Non Patent Document 4):

$$L^l_k = L^{ls}_k + M^l_{k,k-1} + M^l_{k,k+1} \tag{16}$$

The self inductance $L^{ls}_k$ of the linear conductor 301 having $w_k$ in width and $l$ in length, is expressed by the formula (17):

[Formula 17]

$$L^{ls}_k = \frac{\mu_0 l}{2\pi}\left(\ln\left(\frac{2l}{w_k} + \frac{1}{2}\right)\right) \quad (17)$$

In addition, the mutual inductance $M^l_{k,k-1}$, $M^l_{k,k+1}$ are expressed by the formula (18) and the formula (19), respectively:

[Formula 18]

$$M^l_{k,k-1} = 2l\left(\ln\left(\frac{l}{d_{k,k-1}} + \sqrt{1 + \frac{l^2}{d^2_{k,k-1}}}\right) - \sqrt{1 + \frac{d^2_{k,k-1}}{l^2}} + \frac{d_{k,k-1}}{l}\right) \cdot \frac{1 - \exp(-j\Delta\theta_{k-1})}{\exp(j\Delta\theta_k) - 1} \quad (18)$$

[Formula 19]

$$M^l_{k,k+1} = 2l\left(\ln\left(\frac{l}{d_{k,k+1}} + \sqrt{1 + \frac{l^2}{d^2_{k,k+1}}}\right) - \sqrt{1 + \frac{d^2_{k,k+1}}{l^2}} + \frac{d_{k,k+1}}{l}\right) \cdot \frac{\exp(j\Delta\theta_{k+1}) - 1}{1 - \exp(-j\Delta\theta_k)} \quad (19)$$

Here, $d_{k,k-1}$ represents distance between two linear conductors 301 positioned at the k-th and the (k−1)th when counted from the y-axis 202, in the circumferential direction of the elliptical loop conductor 302 in clockwise, and it is expressed by the formula (20):

[Formula 20]

$$d_{k,k-1} = \sqrt{a^2(\sin\phi_k - \sin\phi_{k-1})^2 + b^2(\cos\phi_k - \cos\phi_{k-1})^2} \quad (20)$$

In addition, $\phi k$ is expressed by the formula (21):

[Formula 21]

$$\phi_k = \sum_{i=1}^{k} \frac{\Delta\theta_i + \Delta\theta_{i+1}}{2} \quad (21)$$

On the other hand, $d_{k,k+1}$ indicates distance between two linear conductors 301, the k-th linear conductor and the (k+1)th linear conductor counted from the y-axis 202 in the circumferential direction of the elliptical loop conductor 302 in clockwise, and it is expressed by the formula (22):

[Formula 22]

$$d_{k,k+1} = \sqrt{a^2(\sin\phi_k - \sin\phi_{k+1})^2 + b^2(\cos\phi_k - \cos\phi_{k+1})^2} \quad (22)$$

As described above, equivalent inductance $L^l_k$ (k=1, 2, . . . , N+1) is determined by the dimension of the linear conductor 301, the major axis a and the minor axis b of the elliptical loop conductor 302, and the electrical phase difference $\Delta\theta_k$ (k=1, 2, . . . , N+1).

According to the formula (3) and the formula (5), the equivalent inductances $L^l_k$ and $L^l_{k+1}$ of the adjacent two linear conductors 301 have a relationship of $L^l_k > L^l_{k+1}$. Therefore, distance between the linear conductors 301 (distance between the centers in the width direction of the linear conductors 301) increases from the y-axis 202 in the circumferential direction of the elliptical loop conductor 302 in clockwise. In other words, it increases from the minor axis direction to the major axis direction. In addition, the width $w_k$ of the linear conductor 301 has a tendency to increase in the circumferential direction of the elliptical loop conductor 302 in clockwise from the y-axis 202, in other words, from the minor axis direction to the major axis direction.

In addition, the equivalent inductance $L^r_k$ of the arcuate conductor 303 is expressed by the following formula (23):

[Formula 23]

$$L^r_k = \frac{\mu_0 l^r_k}{2\pi}\left(\ln\left(\frac{2l^r_k}{w^r} + \frac{1}{2}\right)\right) \quad (23)$$

Here, the length and the width of the arcuate conductor 303 are represented by $l^r_k$ and $w_r$, respectively.

The length $l^r_k$ of the arcuate conductor 303 is expressed by the formula (24):

[Formula 24]

$$l^r_k = \int_{\phi_{k-1}}^{\phi_k} \sqrt{1 - \left(\frac{a^2 - b^2}{b^2}\right)\sin^2\varphi}\, d\varphi \quad (24)$$

As thus described, the equivalent inductance $L^r_k$ (k=1, 2, . . . , N+1) of the arcuate conductor 303 is determined by the dimension of the arcuate conductor 303, the major axis a and the minor axis b of the elliptical loop conductor, and the electrical phase difference $\Delta\theta_k$ (k=1, 2, . . . , N+1).

Accordingly, the value of $\Delta\theta_k$ (k=1, 2, . . . , N+1) is obtained by solving the formula (2), formula (3), formula (4), formula (5) and formula (6). It is to be noted that the formula (5) and the formula (6) are solved, by substituting the equivalent inductance $L^l_k$ of the linear conductor 301 and the equivalent inductance $L^r_k$ of the arcuate conductor 303 which are obtained by using the formulas from (17) to (24).

The formula (2) and the formula (3) are prerequisites that are considered as indispensable due to the following reasons.

Figure 6:
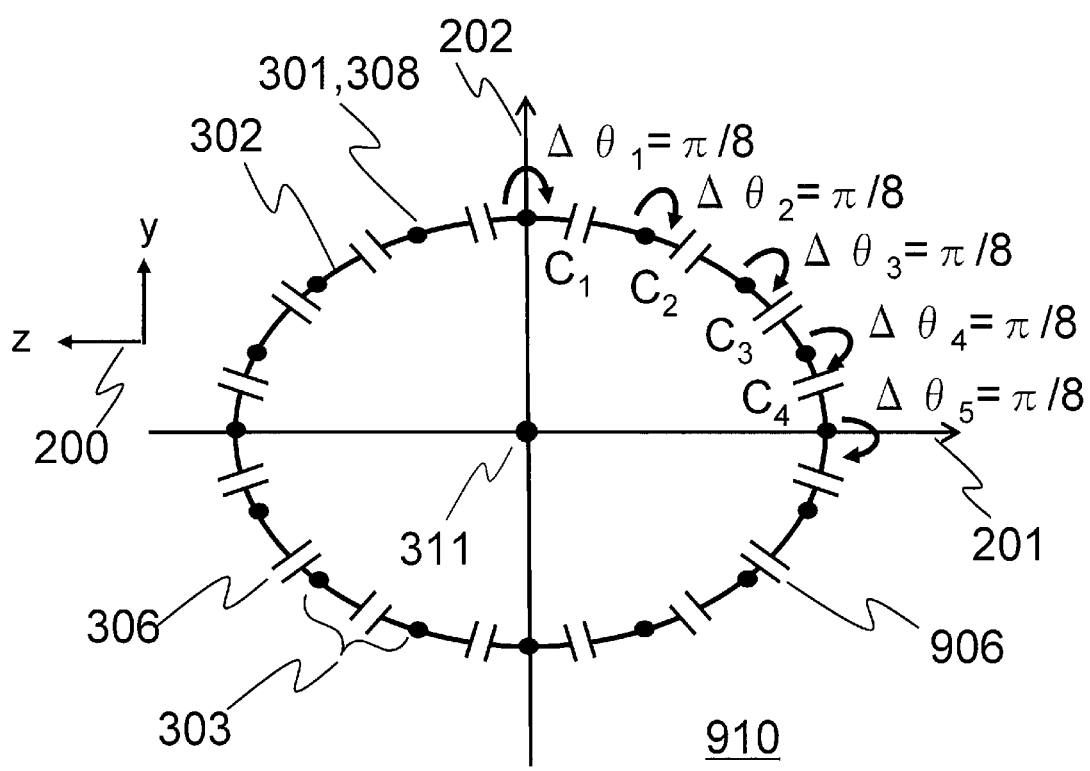
FIG. 6 illustrates an elliptical birdcage coil.

FIG. 6 illustrates the elliptical birdcage coil 910 disclosed by the Non Patent Document 4, in which the values of the capacitors are different from one another. In this kind of elliptical birdcage coil 910, a shift amount of the electrical phase (electrical phase difference) $\Delta\theta$ between each of the loops 309 made up of two linear conductors 301 and two arcuate conductors 303 is adjusted to be constant, in order that the sensitivity distribution in the elliptical birdcage coil gets into homogeneous resonant mode. In other words, values of the respective capacitors are adjusted to establish the following; $\Delta\theta_1 = \Delta\theta_2 = \Delta\theta_3 = \Delta\theta_4 = \pi/8$.

The size of the elliptical birdcage coil 910 as shown in FIG. 6 was configured to be 300 mm in the major axis diameter, 240 mm in the minor axis diameter, and 300 mm in length, and the elliptical birdcage coil 910 was adjusted to establish the resonant mode where the sensitivity distribution was homogeneous at 120 MHz. As a result, the values ($C_1$ to $C_4$) of the respective capacitors shown in FIG. 6 became as the following; $C_1$=29 pF, $C_2$=26.3 pF, $C_3$=23.7 pF, and $C_4$=21.2 pF, and each value of the capacitors 906 showed a trend to increase in the circumferential direction of the elliptical loop conductor 302 in anti-clockwise from the x-axis 201. This indicates that if the electrical phase difference Δθ is constant, the values of the capacitors are not identical.

In the elliptical birdcage coil 910 as shown in FIG. 6, in order to make the vales of the capacitor 906 to be constant, it is necessary to eliminate the condition that the electrical phase difference (the shift amount of electrical phase) is constant. By way of example, if the values of all the capacitors 906 are made to agree with an average value of $C_1$ to $C_4$, it is necessary that the values of $C_1$ and $C_2$ are decreased, and the values of $C_3$ and $C_4$ are increased. A typical birdcage coil shows a trend that when $C_i$ is increased, $\Delta\theta_i$ decreased, and when $C_i$ is decreased, $\Delta\theta_i$ is increased. Therefore, in order to make the values of the capacitor to be constant, it is necessary to satisfy the condition that $\Delta\theta_1<\Delta\theta_2<\Delta\theta_3<\Delta\theta_4$. In other words, the prerequisites of the formula (2) and the formula (3) are indispensable.

Next, when the linear conductors 301 are arranged in such a manner as satisfying the formula (1), and each of the constitutional elements are adjusted and determined so that the electrical phase difference $\Delta\theta_k$ between the adjacent arcuate conductors 303 satisfies the aforementioned formula (2), formula (3) and formula (4), the RF coil unit 310 of the present embodiment becomes the resonant state at the magnetic resonance frequency ($f_c$) while keeping the values of the first capacitors 306 to be constant, and resonance occurs in the resonant mode where the sensitivity distribution of the coil is homogeneous.

As shown in the Non Patent Document 1, when the birdcage coil having N' rungs is activated in the resonant mode in which the sensitivity distribution is homogeneous, the current flowing in the k-th loop of N' loops made up of two adjacent rung conductors and ring conductors therebetween is expressed by the following formula (25):

$$I_k = A \cdot \exp(j(\omega_c t + \theta_k)) \quad (25)$$

On this occasion, the phase $\theta_k$ satisfies the following formula (26):

[Formula 26]

$$\sum_{k=1}^{N'} (\theta_k - \theta_{k-1}) = 2\pi \quad (26)$$

Here, $\theta_k > \theta_{k-1}$, $\theta_0 = \theta_{N'}$, and $\omega_c$ represents angular frequency of the magnetic resonance frequency, and A represents a constant determined by loss of coil and feeding voltage.

The formula (25) indicates that a phase difference of $\Delta\theta_k = \theta_k - \theta_{k-1}$ is generated in the flowing current, between the adjacent two loops. The formula (26) indicates that the phase of the current flowing on the ring conductor is changed by 360 degrees, after going round along the ring conductor. The condition of the formula (26) is also applicable to the case of the elliptical birdcage coil.

The linear conductors 301 of the RF coil unit 310 as shown in FIG. 3A and FIG. 3B are each arranged in line-symmetric relationship with respect to the major axis and the minor axis of the elliptical loop conductor 302. According to the symmetric property of the shape, if the change in the electrical phase on the elliptical loop conductor 302 in the first quadrant 211 as shown in FIG. 3B is 90 degrees, it goes round along the ring conductor (elliptical loop conductor 302), changing by 360 degrees, thereby achieving the resonant mode in which the sensitivity distribution is homogeneous.

A sum of the phase differences Δθ of the loop current 312 flowing in each of the loops 309 in the first quadrant is expressed by the formula (27):

[Formula 27]

$$\frac{\Delta\theta_1}{2} + \sum_{k=2}^{N} \Delta\theta_k + \frac{\Delta\theta_{N+1}}{2} = \frac{\pi}{2} \quad (27)$$

It is to be noted that the phase difference Δθ of the loop current 312 is generated between the adjacent loops 309. Therefore, as for the phase differences on both edges (the phase difference $\Delta\theta_1$ generated placing the y-axis 202 therebetween and the phase difference $\Delta\theta_{N+1}$ generated placing the x-axis 201 therebetween), a half value is added as to each edge, according to the symmetric property of the coil shape.

When the second term in the left part of the formula (27) is modified as a sum of $(\Delta\theta_k+\Delta\theta_{k+1})/2$, the aforementioned formula (4) is obtained. In other words, since the RF coil unit 310 of the present embodiment is configured in such a manner as satisfying the formula (4), as described above, it may be said that N−1 linear conductors 301 in the first quadrant 211 are connected at the positions which establish the electrical phase change of 90 degrees on the elliptical loop conductor 302. Therefore, since 4N linear conductors 301 are located at the positions going round by 360 degrees along the ring conductor (elliptical loop conductor 302), the RF coil unit 310 of the present embodiment resonates in the resonant mode in which the sensitivity distribution is homogeneous when resonance occurs at the magnetic resonance frequency ($f_c$).

As described above, in the RF coil unit 310 of the present embodiment, the electrical phase difference in the loop current 312 flowing in the adjacent two loops 309 is set in such a manner that the difference increases as going away from the y-axis 202 toward the direction of the x-axis 201, and according to the symmetric property of the RF coil unit 310, the electrical phase difference $\Delta\theta_k$ is set in such a manner that the electrical phase difference is 180 degrees, between the two arcuate conductors 303 located at point-symmetrical positions with respect to the original point.

Next, an explanation will be made as to the RF coil unit 310 having been adjusted as described above, operating as the transceive RF coil 105.

Firstly, according to a control signal from the sequencer 119, the transmit/receive switching unit 115 is switched to transfer a signal from the RF magnetic field generator 113 to the RF coil unit 310. When an RF signal including the magnetic resonance frequency ($f_c$) as a carrier wave component is transferred from the RF magnetic field generator 113 to the QD hybrid via the transmit/receive switching unit 115, the QD hybrid distributes the RF signal into two, shifting one electrical phase by 90 degrees, and inputs thus split signals respectively into the first feeding port 304 and the second feeding port 305.

When an RF signal including the magnetic resonance frequency ($f_c$) as the carrier wave component is applied to the first feeding port 304, the RF coil unit 310 becomes the resonant state. On this occasion, the electrical phase of the RF current flowing on the elliptical loop conductor 302 is changed by 360 degrees after going round along the elliptical loop conductor 302. The electrical phase difference between the two feeding ports (the first feeding port 304 and the second feeding port 305) is 75 to 105 degrees. Therefore, when power is fed to one feeding port, the amplitude of the RF current flowing in the elliptical loop conductor 302 is minimized at the other feeding port. Therefore, RF signals are applied to the first feeding port 304 and the second feeding port 305 of the RF coil unit 310 without any interference with each other, allowing the RF coil unit 310 to irradiate the inside of the coil with a rotating magnetic field.

After the irradiation of the rotating magnetic field, a magnetic resonance signal is generated. On this occasion, according to the control signal from the sequencer 119, the transmit/receive switching unit 115 is switched in such a manner as transferring the signal to the receiver 114. According to the reciprocity theorem, the RF coil unit 310 is given a sensitivity distribution similar to that of irradiation time, and detects the magnetic resonance signal. The magnetic resonance signal being detected is transferred via the first feeding port 304 and the second feeding port 305, to the QD hybrid, and one signal is shifted by 90 degrees to be combined with the other. The signal being combined is transferred to the receiver 114, passing through the transmit/receive switching unit 115.

As thus described so far, the RF coil unit 310 operates as the transceive RF coil 105.

As discussed above according to the present embodiment, in the elliptical birdcage coil, the linear conductors are arranged in such a manner that the electrical phase difference between two adjacent arcuate conductors becomes smaller as being distant from the major axis of the elliptical loop conductor. In addition, the linear conductors are arranged in such a manner that a total of the electrical phase difference between the arcuate conductors is 90 degrees in the portion from the major axis to the minor axis. In other words, according to the symmetric property of the elliptical birdcage coil, two arcuate conductors positioned point-symmetrically with respect to the original point are arranged so that the electrical phase difference of the two arcuate conductors becomes 180 degrees.

By arranging the linear conductors as described above, according to the present embodiment, even though each of the first capacitors has identical capacitance, it is possible to achieve the elliptical birdcage coil in which resonance occurs at the magnetic resonance frequency ($f_c$), and it occurs in a resonant mode in which the sensitivity distribution of the coil is homogeneous upon resonation.

Therefore, according to the present embodiment, it is possible to provide the elliptical birdcage coil with capacitors being inserted, each having identical capacitance. With this configuration, time and effort upon manufacturing, production cost, and a swell of variations in coil performance of the elliptical birdcage coil may be reduced.

It is to be noted that in the RF coil unit 310 as shown in FIG. 3A and FIG. 3B, two linear conductors 301 are arranged on the x-axis 201, and two linear conductors 301 are arranged on the y-axis 202. However, the arrangement of the linear conductor 301 is not limited to this manner. It is only required that 4N linear conductors 301 are arranged in such a manner as being symmetrical with respect to the x-axis 201 and the y-axis 202.

Figure 7A:
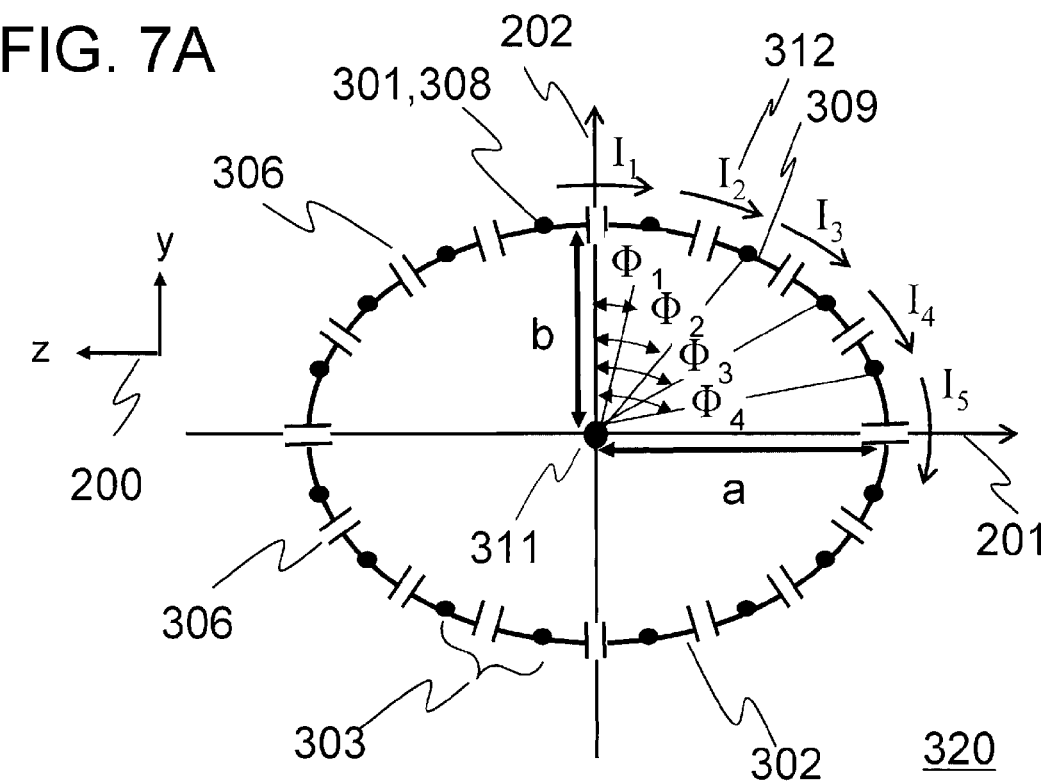
FIG. 7A illustrates a modification example of the RF coil unit according to the first embodiment.
Figure 7B:
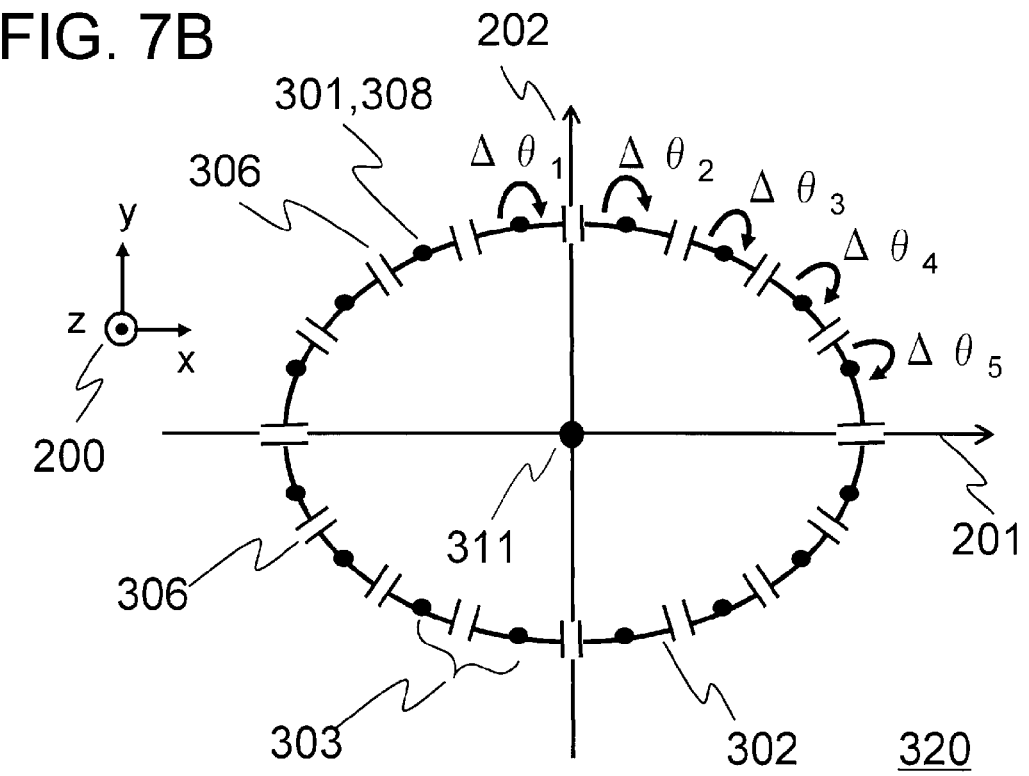
FIG. 7B illustrates a modification example of the RF coil unit according to the first embodiment.

FIG. 7A and FIG. 7B show one example of the RF coil unit 320 in which the linear conductors 301 are arranged neither on the x-axis 201 nor on the y-axis 202. Basically, also in the RF coil unit 320, the linear conductors 301 are arranged in such a manner as being line-symmetrical with respect to the x-axis 201 and the y-axis 202, respectively, and N linear conductors 301 are arranged in each of the quadrants that are defined by the x-axis 201 and the y-axis 202.

Also in this case, the first capacitors 306 are arranged one by one respectively on the arcuate conductors 303, and the capacitance of each capacitor is assumed as identical. Then, it is adjusted in such a manner that the RF coil unit 320 becomes the resonance state at the magnetic resonance frequency ($f_c$) that is used in the transceive RF coil 105.

In addition, the first feeding port 304 and the second feeding port 305 are arranged at the positions line-symmetrical with respect to the y-axis 202 or the x-axis 201, and they are positioned respectively in such a manner that when power is fed to one feeding port, the amplitude of the RF current flowing in the other feeding point is minimized.

In the N linear conductors 301 in the first quadrant 211, as shown in FIG. 7A, their connection points 308 are arranged in such a manner that the angle $\Phi_m$ (m=1, 2, . . . , N) formed by the y-axis 202 satisfies the following formula (28):

[Formula 28]

$$\Phi_m = \tan^{-1}\left(\frac{b}{a}\tan\left(\frac{\Delta\theta_2}{2} + \sum_{k=0}^{m-1}(1-\delta_0)\frac{\Delta\theta_{k+1}+\Delta\theta_{k+2}}{2}\right)\right) \quad (28)$$

Here, $\Delta\theta_k$ represents, in the first quadrant 211, the electrical phase difference ($\Delta\theta_k = \theta_k - \theta_{k-1}$) that is a difference between the phase $\theta_k$ of the loop current 312 flowing in the k-th loop 309 counted starting from near the y-axis 202, and the phase $\theta_{k-1}$ of the loop current 312 flowing in the (k−1)th loop 309. Here, the phase of the loop current 312 flowing in the loop 309 adjacent to the arcuate conductor 303 crossing the y-axis 202 in the second quadrant is represented by $\theta_0$, and the phase of the loop current flowing in the loop 309 adjacent to the arcuate conductor 303 crossing the x-axis 201 in the fourth quadrant is represented as $\theta_N$. The linear conductors 301 in the other quadrants are arranged at the positions line-symmetrical with respect to the x-axis 201 and the y-axis 202 as a whole of the RF coil unit 320, as described above.

In the RF coil unit 320, the electrical phase difference $\Delta\theta_k$ is adjusted in such a manner as satisfying the aforementioned formula (2), formula (3), formula (29), formula (30), and formula (31), similar to the RF coil unit 310. According to the symmetric property of the coil shape, the electrical phase differences $\Delta\theta_1$ becomes equal to $\Delta\theta_2$; $\Delta\theta_1$ and $\Delta\theta_2$ representing the differences between the loop 309 of the arcuate conductor 303 crossing the y-axis 202, and each of the loops on both sides, respectively:

[Formula 29]

$$\sum_{k=2}^{N+1} \Delta\theta_k = \frac{\pi}{2} \quad (29)$$

[Formula 30]

$$\sin(\Delta\theta_{k+1}) = \frac{L_{k-1}^l}{L_k^l}\sin(\Delta\theta_k) \quad (30)$$

[Formula 31]

$$\cos(\Delta\theta_{k+1}) = 1 + \frac{1}{L_k^l}((L_k^r - L_{k-1}^r) + L_{k-2}^l(\cos(\Delta\theta_{k-1}) - 1)) \quad (31)$$

Here, k is an integer, satisfying N+1>k>1. In the first quadrant 211 as shown in FIG. 7B, $L^r_m$ (m=1, 2, . . . , N+1) indicates equivalent inductance of the arcuate conductor 303 being the m-th counting from the y-axis 202 in the circumferential direction of the elliptical loop conductor 302 in clockwise, and $L^l_m$ (m=1, 2, . . . , N) indicates equivalent inductance of the linear conductor 301 being the m-th counting from the y-axis 202 in the circumferential direction of the elliptical loop conductor 302 in clockwise.

Figure 8:
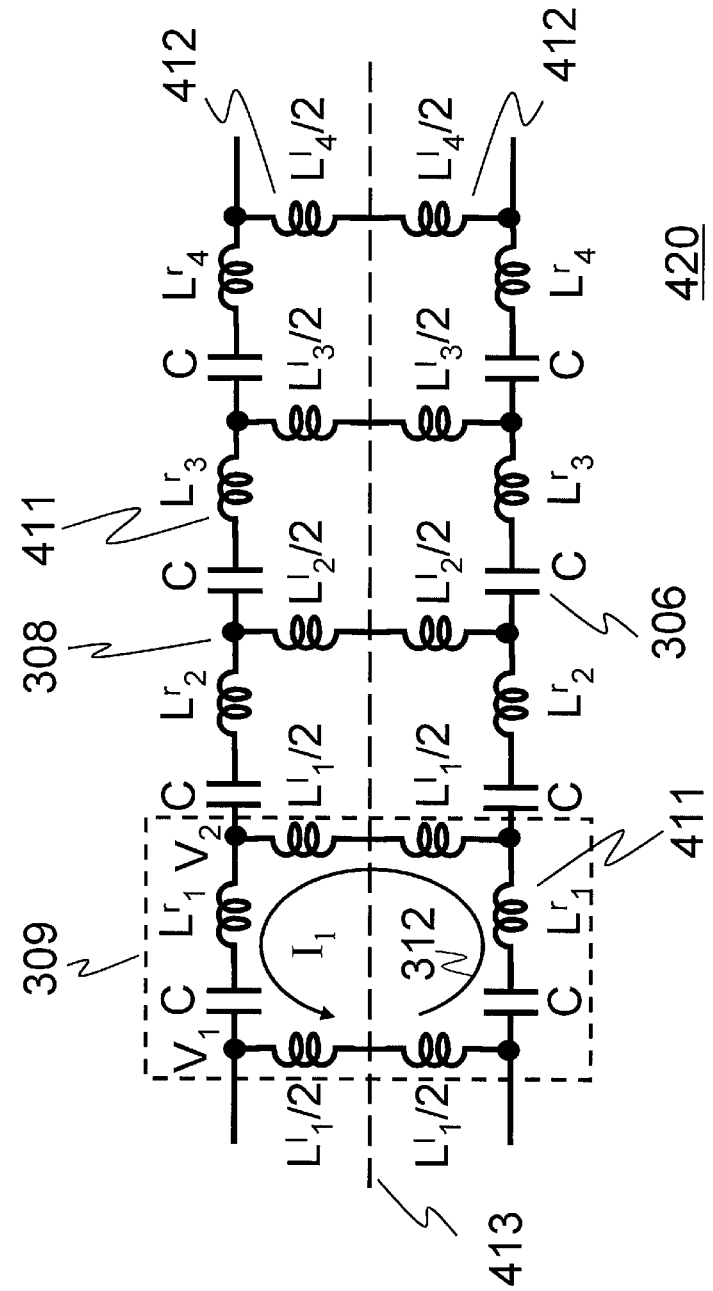
FIG. 8 is a circuit diagram illustrating a partial equivalent circuit in the modification example of the RF coil according to the first embodiment.

The formula (30) and the formula (31) are obtained, being derived from the equivalent circuit 420 of the RF coil unit 320 in the first quadrant 211 as shown in FIG. 7B. FIG. 8 illustrates this equivalent circuit 420. FIG. 8 illustrates the RF coil unit 320 in the form of equivalent circuit, by developing the first quadrant part in the plane. A value of the first capacitor 306 is represented by C. Since the equivalent circuit 410 is symmetrical with respect to the vertical direction of FIG. 8 on paper, a virtual ground 413 is taken as a middle point of the linear conductor 301.

The voltage $V_k$ between the connection point 308 of the k-th linear conductor 301 counting from the y-axis 202 in the circumferential direction of the elliptical loop conductor 302 in clockwise, and the virtual ground 413 is represented by the formula (32) according to the Kirchhoff's circuit laws:

[Formula 32]

$$V_k = j\omega L^l_{k-1}(I_k - I_{k-1})/2 \qquad (32)$$

Here, $I_k$ represents the loop current 312 flowing in the k-th loop 309 counted starting from near the y-axis 202 in the first quadrant 211.

In addition, a difference between the voltage $V_{k+1}$ and the voltage $V_k$ is represented by the formula (33) according to the equivalent circuit 420 as shown in FIG. 8:

[Formula 33]

$$V_{k+1} - V_k = \left(j\omega L^r_{k-1} + \frac{1}{j\omega C}\right)I_k \qquad (33)$$

Here, when the formula (32) is substituted into the formula (33), the formula (34) is obtained:

[Formula 34]

$$\frac{2}{\omega^2 C} = 2L^r_k - L^l_k\left(\frac{I_{k+1}}{I_k} - 1\right) - L^l_{k-1}\left(\frac{I_{k-1}}{I_k} - 1\right) \qquad (34)$$

Here, $I_k$ being the loop current 312 is expressed by the formula (35):

$$I_k = A \cdot \exp(j(\omega t + \theta_k)) \qquad (35)$$

In addition, since $\Delta\theta_k = \theta_k - \theta_{k-1}$, $I_{k+1}/I_k$ and $I_k/I_{k-1}$ are expressed by the following formula (36) and formula (37):

$$I_{k+1}/I_k = \exp(j\Delta\theta_{k+1}) \qquad (36)$$

$$I_k/I_{k-1} = \exp(j\Delta\theta_k) \qquad (37)$$

When the formula (34) is modified by using those elements above, the formula (34) is expressed by the next formula (38):

[Formula 38]

$$\frac{2}{\omega^2 C} = 2L^r_k - L^l_k(\exp(j\Delta\theta_{k+1}) - 1) - L^l_{k-1}(\exp(-j\Delta\theta_k) - 1) \qquad (38)$$

Here, a value of the first capacitor 306 is represented by C, and it is constant. The resonant angular frequency of the coil is represented by ω, and it is constant, independent of k.

By using the formula that is obtained by substituting k−1 into k in the formula (38) together with the formula (38), a solution is obtained as to $\Delta\theta_{k+1}$, and then, the formula (39) is obtained:

[Formula 39]

$$\exp(j\Delta\theta_{k+1}) = \frac{1}{1 + \dfrac{2(L^r_k - L^r_{k+1}) + j2L^l_{k-1}\sin(\Delta\theta_k) + L^l_{k-2}(\exp(-j\Delta\theta_{k-1}) - 1)}{L^l_k}} \qquad (39)$$

When the formula (39) is solved as to the real part, the formula (31) is obtained. In addition, when the formula (39) is solved as to the imaginary part, the next formula (40) is obtained:

[Formula 40]

$$\sin(\Delta\theta_{k+1}) = \frac{2L^l_{k-1}}{L^l_k}\sin(\Delta\theta_k) - \frac{L^l_{k-2}}{L^l_k}\sin(\Delta\theta_{k-1}) \qquad (40)$$

Here, $L^l_0$ indicates the inductance of the linear conductor being the closest to the y-axis 202 in the second quadrant as shown in FIG. 7B, and it becomes equal to $L^l_1$ according to the symmetric property of the coil shape. In addition, $\Delta\theta_0$ also becomes equal to $\Delta\theta_3$ according to the symmetric property of the coil shape, and $\Delta\theta_1$ also becomes equal to $\Delta\theta_2$. Therefore, when the formula (40) for the case of k=2 is modified, considering that $L^l_0 = L^l_1$, $\Delta\theta_0 = \Delta\theta_3$, and $\Delta\theta_1 = \Delta\theta_2$, the formula (30) for the case where k=2 is obtained.

When the formula substituting k−1 into k of the formula (30) is substituted into the second term on the right side of the formula (40), the formula (40) becomes equivalent to the formula (30).

Next, an explanation will be made as to a method for calculating the equivalent inductance $L^l_m$ and $L^r_m$ of the linear conductor 301 and the elliptical loop conductor 302 (arcuate conductor 303) that are used in the formula (30) and the formula (31).

Similar to the case of the RF coil unit 310, the equivalent inductance $L^l_k$ of the linear conductor 301 in the RF coil unit 320 is obtained as a sum of the self inductance $L^{ls}_k$ obtained from the shape of the linear conductor 301 and mutual inductance $M^l_{k,k-1}$, and $M^l_{k,k+1}$ between the adjacent linear conductors 301. In other words, it is expressed by the formula (16). Then, the self inductance $L^{ls}_k$ of the linear conductor 301 having $w_k$ in width and l in length, and the mutual inductance $M^l_{k,k-1}$, $M^l_{k,k+1}$ are expressed by the formula (17) to the formula (22). It is to be noted that the variable $\phi_k$ of the formula (20) is expressed by the formula (41):

[Formula 41]

$$\phi_k = \frac{\Delta\theta_1}{2} + \sum_{i=0}^{k-1}(1 - \delta_0)\frac{\Delta\theta_i + \Delta\theta_{i+1}}{2} \qquad (41)$$

As thus described, also in the RF coil unit 320, the equivalent inductance $L^l_k$ (k=1, 2, . . . , N) is determined by the dimension of linear conductor 301, the major axis a and the minor axis b of the elliptical loop conductor, and $\Delta\theta_k$ (k=1, 2, . . . , N+1).

In addition, the equivalent inductance $L^r_k$ of the arcuate conductor 303 is expressed by the formula (23), and the length $l^r_k$ of the arcuate conductor 303 is expressed by the formula (24). It is to be noted that if k=1, it is expressed by the formula (42), and if k=N+1, it is expressed by the formula (43):

[Formula 42]

$$l^r_1 = 2\int_0^{\phi_1} \sqrt{1-\left(\frac{a^2-b^2}{b^2}\right)\sin^2\varphi}\, d\varphi \qquad (42)$$

[Formula 43]

$$l^r_{N+1} = 2\int_{\phi_N}^{\frac{\pi}{2}} \sqrt{1-\left(\frac{a^2-b^2}{b^2}\right)\sin^2\varphi}\, d\varphi \qquad (43)$$

Therefore, also in the RF coil unit 320, the equivalent inductance $L^r_k$ (k=1, 2, . . . , N+1) of the arcuate conductor 303 is determined by the dimension of the arcuate conductor 303, the major axis a and the minor axis b of the elliptical loop conductor, and $\Delta\theta_k$ (k=1, 2, . . . , N+1).

Accordingly, the value of $\Delta\theta_k$ (k=1, 2, . . . , N+1) is obtained by solving the formula (30) and the formula (31) substituting the equivalent inductance $L^l_k$ of the linear conductor 301 and the equivalent inductance $L^r_k$ of the arcuate conductor 303, each having $\Delta\theta_k$ (k=1, 2, . . . , N+1) as variables, under satisfying the formula (2), the formula (3), and the formula (29).

Next, there will be described in the following that the RF coil unit 320 having the configuration above becomes the resonant state at the magnetic resonance frequency ($f_c$), and resonance occurs in the resonant mode in which the sensitivity distribution of the coil is homogeneous.

Also in the RF coil unit 320, similar to the case of the RF coil unit 310 as shown in FIG. 3A and FIG. 3B, if the change in electrical phase is 90 degrees on the elliptical loop conductor 302 in the first quadrant 211 as shown in FIG. 7B, the resonant mode where the sensitivity distribution is homogeneous is established. In other words, it is only required that a sum of the phase differences $\Delta\theta$ of the loop current 312 flowing in the loops 309 in the first quadrant 211 becomes 90 degrees. The phase difference of the loop current $\Delta\theta_k$ occurs between the adjacent loops 309, and therefore the sum of the phase differences $\Delta\theta_k$ is expressed by the formula (29). This indicates that the sum of the electrical phase differences $\Delta\theta$ of the loop current 312 flowing in the loops 309 in the first quadrant 211 is 90 degrees.

Therefore, the RF coil unit 320 as shown in FIG. 7A and FIG. 7B becomes the resonant state at the magnetic resonance frequency ($f_c$), similar to the case of the RF coil unit 310, and resonance occurs in the resonant mode where the sensitivity distribution of the coil is homogeneous.

In addition, the RF coil unit 320 as shown in FIG. 7A and FIG. 7B is provided with 4N linear conductors 301 being arranged at the positions symmetrical with respect to the x-axis 201 and the y-axis 202. However, the number of the linear conductors 301 is not limited to this example. By way of example, the number may be 2N. It is only required that 2N linear conductors 301 are arranged at the positions symmetrical with respect to the x-axis 201 and the y-axis 202.

Figure 9A:
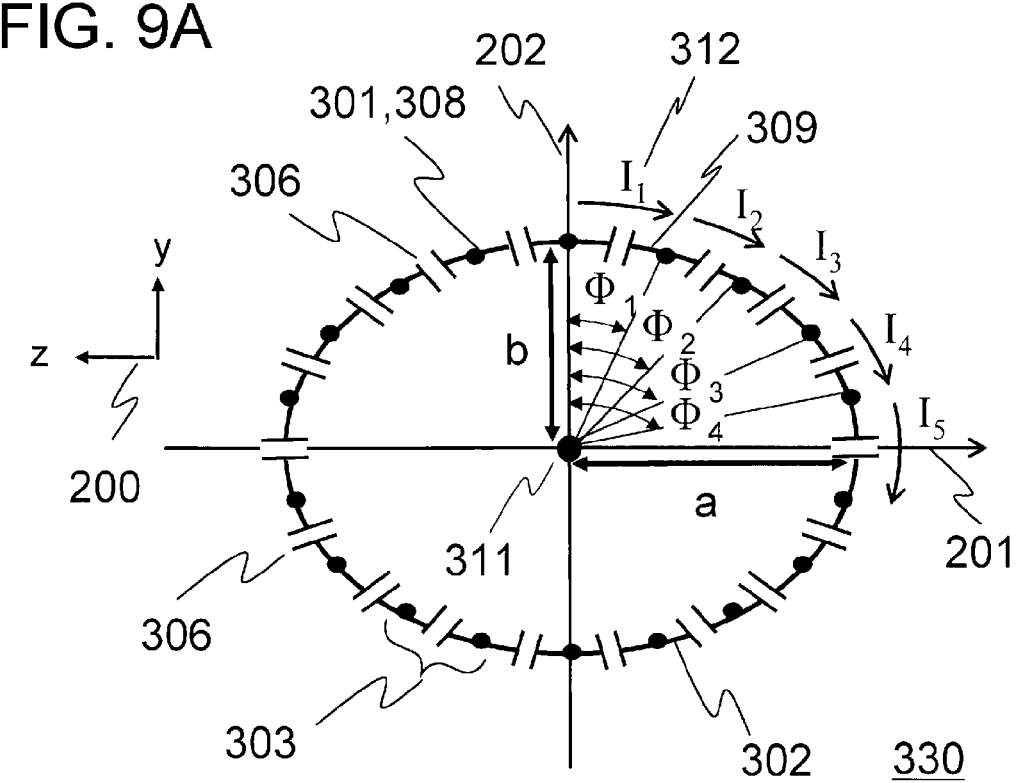
FIG. 9A illustrates a modification example of the RF coil unit according to the first embodiment.
Figure 9B:
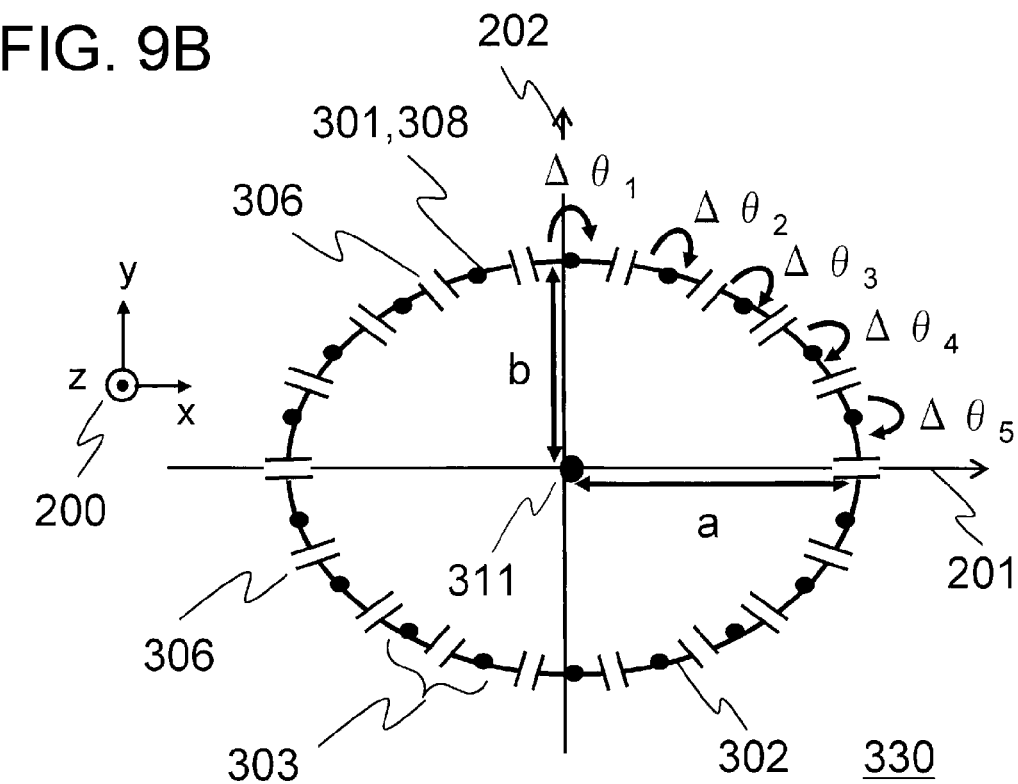
FIG. 9B illustrates a modification example of the RF coil unit according to the first embodiment.

FIG. 9A and FIG. 9B illustrate the RF coil unit 330 provided with 2N linear conductors 301, being arranged at the positions symmetrical with respect to the x-axis 201 and the y-axis 202. There is shown an example in FIG. 9A and FIG. 9B in which the linear conductors 301 are arranged on the y-axis 202, assuming that N=9, and an explanation will be made regarding this case.

Also in this example, the first capacitors 306 are arranged one by one respectively on the arcuate conductors 303, and the capacitance thereof is assumed as identical. Then, it is adjusted so that the RF coil unit 330 becomes resonant state at the magnetic resonance frequency ($f_c$) that is used in the transceive RF coil 105.

In addition, the first feeding port 304 and the second feeding port 305 are positioned line-symmetrically with respect to the y-axis 202 or the x-axis 201, and they are arranged respectively at the positions allowing that when power is fed to one feeding port, the amplitude of the RF current flowing in the other feeding port is minimized.

As shown in FIG. 9A, the N linear conductors 301 are arranged in the first quadrant 211, with the connection points 308 being placed in such a manner that the angle $\Phi_m$ (m=1, 2, . . . , [N/2]) formed by the y-axis 202 satisfies the formula (1), similar to the case of the RF coil unit 310 of the first embodiment. Here, [N/2] represents the integer part of N/2. The linear conductors 301 in the other quadrants, are each arranged at the positions line-symmetrical with respect to the x-axis 201 and the y-axis 202 as a whole of the RF coil unit 330.

In addition, a value of the electrical phase difference $\Delta\theta_k$ is adjusted so that it satisfies the aforementioned formula (2), formula (3), formula (44), formula (5), and formula (45):

[Formula 44]

$$\sum_{k=1}^{[N/2]} \frac{\Delta\theta_k + \Delta\theta_{k+1}}{2} + \frac{\Delta\theta_{[N/2]+1}}{2} = \frac{\pi}{2} \qquad (44)$$

[Formula 45]

$$\cos(\Delta\theta_{k+1}) = 1 + \frac{1}{L^l_{k+1}}((L^r_k - L^r_{k-1}) + L^l_{k-1}(\cos(\Delta\theta_{k-1}) - 1)) \qquad (45)$$

Here, k is an integer satisfying [N/2]+2>k>0. Similar to the RF coil unit 310, $L^r_m$ and $L^l_m$ indicate respectively, equivalent inductance of the arcuate conductor 303, and equivalent inductance of the linear conductor 301.

Figure 10:
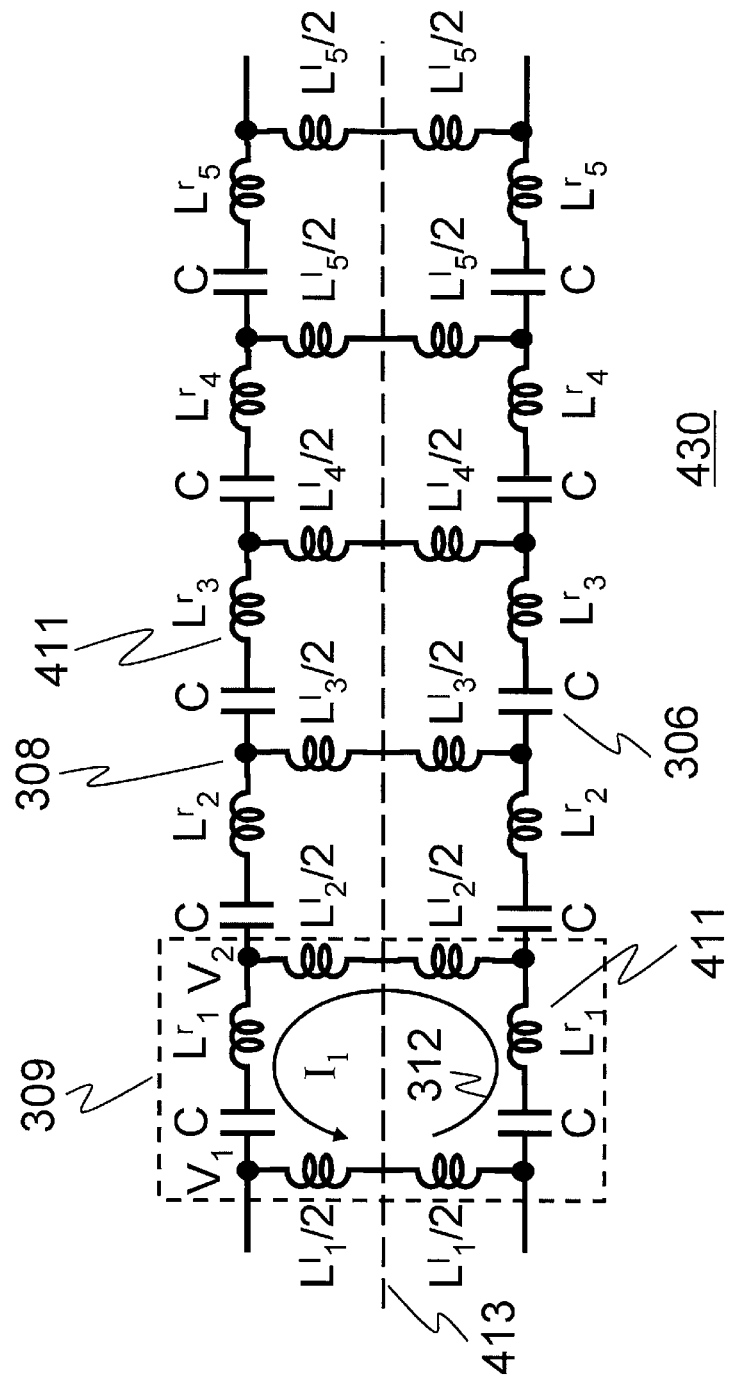
FIG. 10 is a circuit diagram illustrating a partial equivalent circuit in the modification example of the RF coil according to the first embodiment.

The formula (5) and the formula (45) are derived from the equivalent circuit 430 of the RF coil unit 330 in the first quadrant 211 as shown in FIG. 9B. FIG. 10 illustrates this equivalent circuit 430. FIG. 10 illustrates the part of the first quadrant 211 of the RF coil unit 330 that is developed on a plane surface in the form of equivalent circuit. A value of the first capacitor 306 is represented by C. Here, since the equivalent circuit 430 is symmetrical with respect to the vertical direction of FIG. 10 on paper, a virtual ground 413 is taken at the middle point of the linear conductor 301.

The equivalent circuit 430 as shown in FIG. 10 has the same circuit configuration as the equivalent circuit 410 as shown in FIG. 5, except that one more loop 309 is added to the equivalent circuit as shown in FIG. 5. Therefore, according to the Kirchhoff's circuit laws, similar to the case of the RF coil unit 310 as shown in FIG. 3A and FIG. 3B, the formula (5) and the formula (6) are derived. It is to be noted here that in the equivalent circuit 430 as shown in FIG. 10, because of the symmetric property of the coil, this is also applicable in the case where k=[N/2]+1, and the formula (45) is established (N=9 in FIG. 10).

As for the equivalent inductance $L^l_k$ of the linear conductor 301 and the equivalent inductance $L^r_k$ of the arcuate conductor 303, those are expressed by the same formulas as those for the RF coil unit 310, and the range of k becomes [N/2]+2>k>0. It is to be noted that the length of the arcuate conductor 303 under the condition that k=[N/2]+1 is expressed by the following formula (46):

[Formula 46]

$$l^r_{N+1} = 2\int_{\phi_N}^{\frac{\pi}{2}} \sqrt{1-\left(\frac{a^2-b^2}{b^2}\right)\sin^2\varphi}\, d\varphi \tag{46}$$

Therefore, the equivalent inductance $L^l_k$ of the linear conductor 301, and the equivalent inductance $L^r_k$ of the arcuate conductor 303 are determined by the dimension of the arcuate conductor 303, the major axis a and the minor axis b of the elliptical loop conductor 302, and $\Delta\theta_k$ (k=1, 2, ..., [N/2]+1).

Accordingly, the value of $\Delta\theta_k$ (k=1, 2, ..., [N/2]+1) is obtained by solving the formula (5) and the formula (45) substituting the equivalent inductance $L^l_k$ of the linear conductor 301 and the equivalent inductance $L^r_k$ of the arcuate conductor 303, each having $\Delta\theta_k$ (k=1, 2, ..., [N/2]+1) as variables, under satisfying the formula (2), the formula (3), and the formula (44).

Next, there will be described in the following that the RF coil unit 330 having the configuration as described above becomes the resonant state at the magnetic resonance frequency ($f_c$), and resonance occurs in the resonant mode where the sensitivity distribution of the coil is homogeneous.

Also in the RF coil unit 330, similar to the RF coil unit 310 as shown in FIG. 3A and FIG. 3B, when the change of the electrical phase is 90 degrees on the elliptical loop conductor 302 in the first quadrant 211 as shown in FIG. 9B, this establishes the resonant mode where the sensitivity distribution is homogeneous. In other words, it is only required that the sum of the phase differences $\Delta\theta$ of the loop current 312 flowing in the loops 309 in the first quadrant 211 becomes 90 degrees.

The phase difference $\Delta\theta_k$ of the loop current 312 occurs between the adjacent loops 309, and therefore, as the phase difference $\Delta\theta_k$ generated on the y-axis 202 in FIG. 9B, a half value thereof is added according to the symmetric property of the coil shape. As a result, the sum of the phase differences $\Delta\theta_k$ is expressed by the next formula (47):

[Formula 47]

$$\frac{\Delta\theta_1}{2} + \sum_{k=2}^{[N/2]+1} \Delta\theta_k = \frac{\pi}{2} \tag{47}$$

When the formula (47) is modified as the sum of $(\Delta\theta_k+\Delta\theta_{k+1})/2$, the formula (44) is established. This indicates that the sum of the electrical phase differences $\Delta\theta$ of the loop current 312 flowing in the loops 309 in the first quadrant 211 is 90 degrees.

Therefore, the RF coil unit 330 becomes the resonance state at the magnetic resonance frequency ($f_c$), similar to the case of the RF coil unit 310, and resonance occurs in the resonant mode where the sensitivity distribution of the coil is homogeneous.

In the RF coil unit 310, the RF coil unit 320, and the RF coil unit 330, the first capacitor 306 is arranged on the arcuate conductor 303, but the arrangement of the first capacitor 306 is not limited to this example. The first capacitor 306 may be arranged on the linear conductor 301.

Figure 11A:
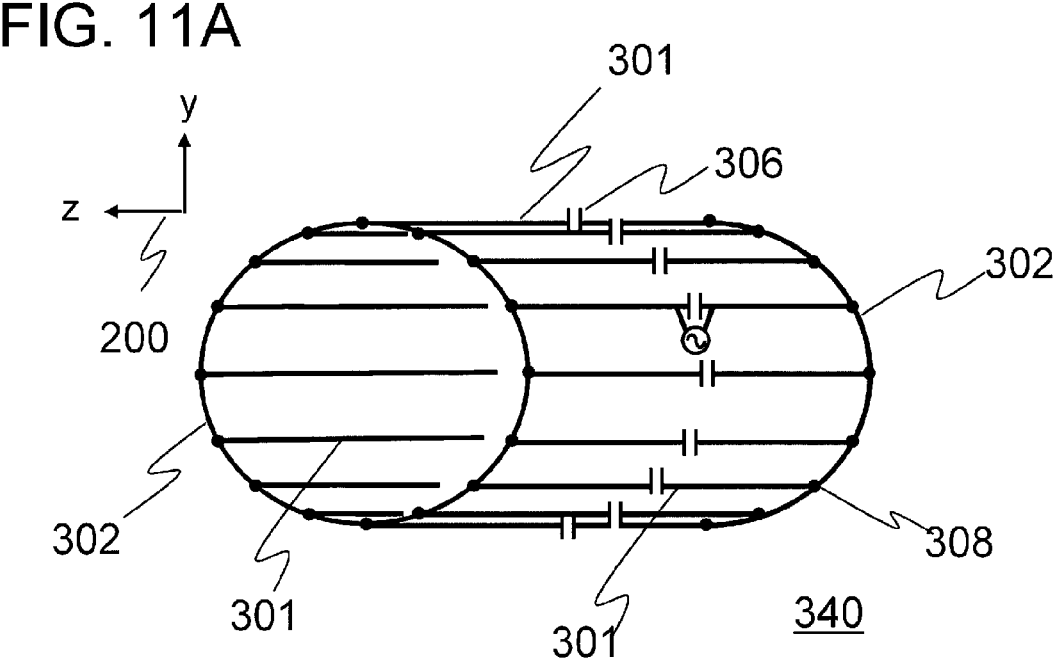
FIG. 11A illustrates a modification example of the RF coil unit according to the first embodiment.
Figure 11B:
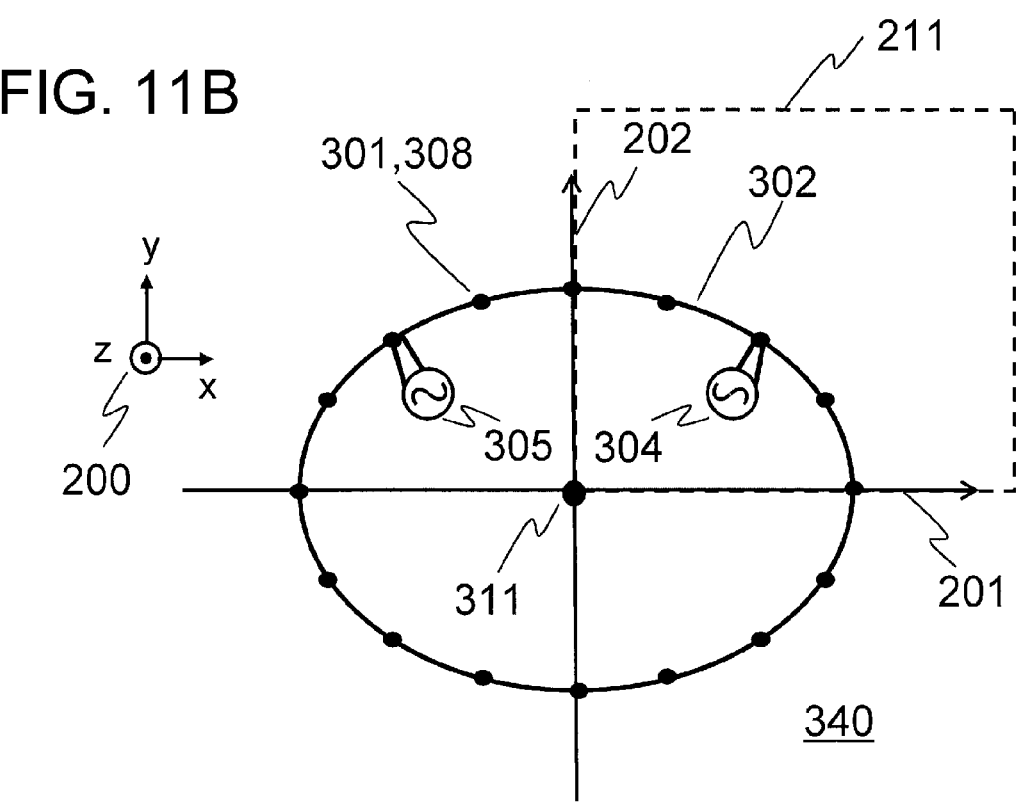
FIG. 11B illustrates a modification example of the RF coil unit according to the first embodiment.

FIG. 11A and FIG. 11B illustrate the RF coil unit 340 in which the first capacitors 306 are arranged on the linear conductors 301. Here, an explanation will be made, taking an example that the linear conductors 301 are arranged in the same manner as the RF coil unit 310. Therefore, the RF coil unit 340 as shown in FIG. 11A and FIG. 11B has the same structure as the RF coil unit 310 shown in FIG. 3A and FIG. 3B, except the points that the first capacitors 306 are arranged on the linear conductors 301 and how the feeding ports are arranged.

The capacitance of all the first capacitors 306 is identical, and it is adjusted so that the RF coil unit 340 becomes the resonant state at the magnetic resonance frequency ($f_c$) that is used in the transceive RF coil 105.

The first feeding port 304 and the second feeding port 305 are placed at the line-symmetrical positions with respect to the y-axis 202 or the x-axis 201, similar to the RF coil unit 310, and they are positioned respectively in such a manner that when power is fed to one feeding port, the amplitude of the RF current flowing in the other feeding point is minimized. It is to be noted that the arranged positions are not on the arcuate conductors 303, but on the linear conductors 301. By way of example, in the RF coil unit 340, specifically, as shown in FIG. 11A and FIG. 11B, those feeding ports are connected respectively to the first capacitors 306 on the two linear conductors 301, being in a line-symmetrical relationship with respect to the y-axis 202, and the electrical phase difference therebetween falls into the range from 75 to 105 degrees.

In the RF coil unit 340, similar to the RF coil unit 310, a value of electrical phase difference $\Delta\theta_k$ between the adjacent loops 309 is adjusted so that the value satisfies the formula (2), the formula (3), and the formula (4), and in addition, the following formula (48) and the formula (49):

[Formula 48]

$$\frac{\sin(\Delta\theta_k)}{\sin(\Delta\theta_{k+1})} = \frac{\omega^2 L^l_{k+1}C - 1}{\omega^2 L^l_k C - 1} \tag{48}$$

[Formula 49]

$$\left(L^l_{k+1} - \frac{1}{\omega^2 C}\right)(\cos(\Delta\theta_{k+1}) - 1) + \left(L^l_k - \frac{1}{\omega^2 C}\right)(\cos(\Delta\theta_k) - 1) = 2L^r_k \tag{49}$$

Here, k is an integer that satisfies N+1>k>0, and k' is an integer that satisfies N>k'>0. In the first quadrant 211 shown in FIG. 3B, $L^r_m$ (m=1, 2, ..., N) indicates the equivalent inductance of the m-th arcuate conductor 303 counting from the y-axis 202 in the circumferential direction of the elliptical loop conductor 302 in clockwise, and $L^l_m$ (m=1, 2, ..., N+1) indicates the equivalent inductance of the m-th linear conductor 301 counting from the y-axis 202 in the circumferential direction of the elliptical loop conductor 302 in clockwise. The equivalent inductance of the linear conductor 301 having the connection point 308 on the y-axis 202 is represented by $L^l_0$.

Figure 12:
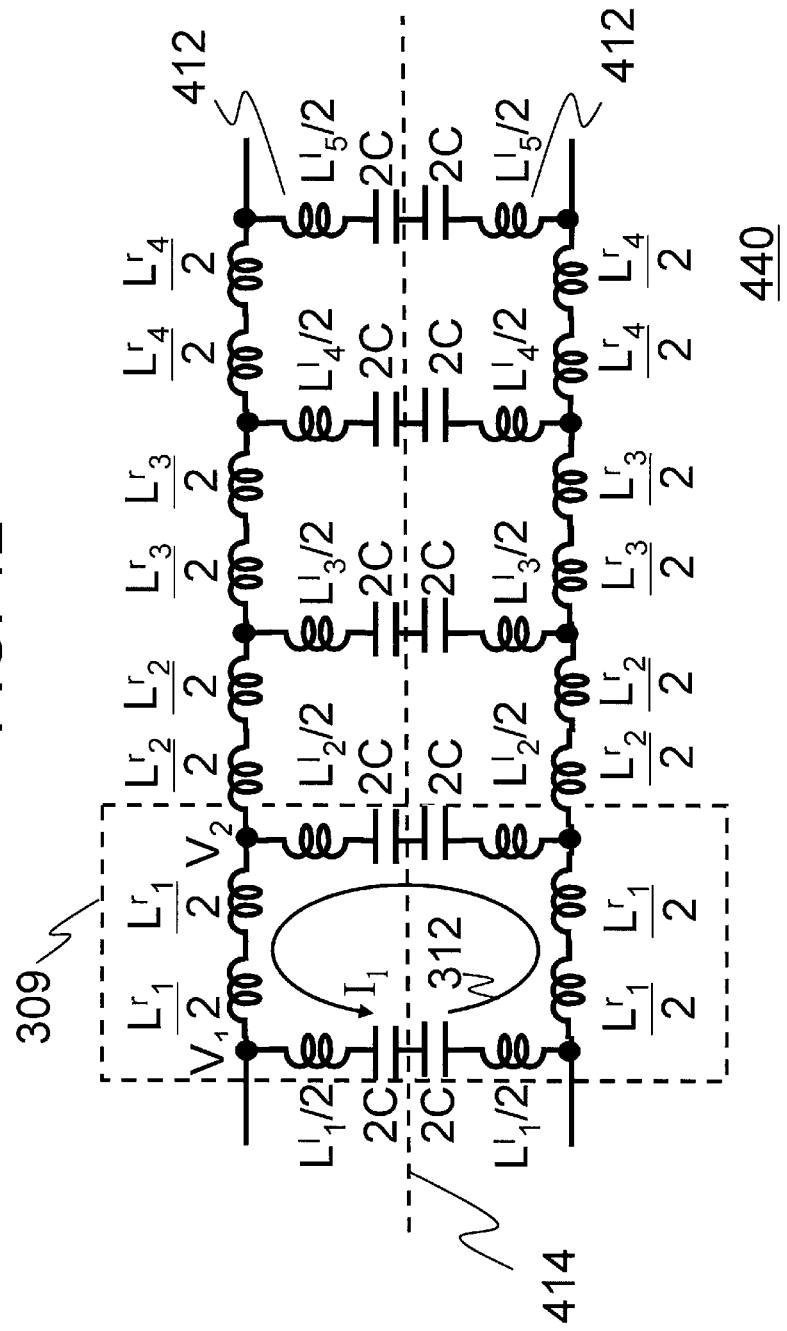
FIG. 12 is a circuit diagram illustrating a partial equivalent circuit in the modification example of the RF coil according to the first embodiment.

The aforementioned formula (48) and formula (49) are derived from the equivalent circuit 440 in the RF coil unit 340 as shown in FIG. 11B. FIG. 12 illustrates this equivalent circuit 440. In the equivalent circuit 440, it is assumed that the first capacitor 306 having the capacitance C corresponds to two capacitors with capacitance 2C, being serially connected. Accordingly, it is possible to assume that the equivalent circuit 440 is symmetrical with respect to the vertical direction of FIG. 12 on paper, and thus a virtual ground 413 is set on the middle point of the linear conductor 301.

The voltage $V_k$ between the connection point 308 of the k-th linear conductor 301 counting from the y-axis 202 in the circumferential direction of the elliptical loop conductor 302 in clockwise, and the virtual ground 413 is represented by the formula (50) according to the Kirchhoff's circuit laws:

[Formula 50]

$$V_k = \frac{1}{2}\left(j\omega L^l_k + \frac{1}{j\omega C}\right) \cdot (I_k - I_{k-1}) \quad (50)$$

Here, $I_k$ represents the loop current 312 flowing in the k-th loop 309 counted starting from near the y-axis 202 in the first quadrant 211.

A difference between the voltage $V_{k+1}$ and the voltage $V_k$ is expressed by the formula (51) according to the equivalent circuit 440 as shown in FIG. 12:

[Formula 51]

$$V_{k+1} - V_k = j\omega L^r_k I_k \quad (51)$$

The formula (52) is obtained from the formula (50) and the formula (51):

[Formula 52]

$$\left(L^l_{k+1} - \frac{1}{\omega^2 C}\right)(\exp(i\Delta\theta_{k+1}) - 1) + \left(L^l_k - \frac{1}{\omega^2 C}\right)(\exp(-i\Delta\theta_k) - 1) = 2L^r_k \quad (52)$$

If a solution is obtained as to the real part in the formula (52), the formula (49) is obtained, and if a solution is obtained as to the imaginary part, the formula (48) is obtained.

Also in the RF coil unit 340, the equivalent inductance $L^l_k$ of the linear conductor 301 and the equivalent inductance $L^r_k$ of the arcuate conductor 303 are obtained by using the formulas from (17) to (24), similar to the case of the RF coil unit 310.

Accordingly, the value of $\Delta\theta_k$ (k=1, 2, . . . , N+1) is obtained by solving the formula (48) and the formula (49) substituting the equivalent inductance $L^l_k$ of the linear conductor 301 and the equivalent inductance $L^r_k$ of the arcuate conductor 303, each having $\Delta\theta_k$ (k=1, 2, . . . , N+1) as variables, under satisfying the formula (2), the formula (3), and the formula (4).

Similar to the RF coil unit 310, the RF coil unit 340 also satisfies the formula (4), and the linear conductors 301 are arranged at the positions, with the change of the electrical phase difference by 360 degrees, after going round along the elliptical loop conductor 302, and therefore, the resonant state is established at the magnetic resonance frequency ($f_c$), and resonance occurs in the resonant mode where the sensitivity distribution of the coil is homogeneous.

It is to be noted that, in this example here, an explanation has been made as to the RF coil unit 340 in which the first capacitors 306 are arranged on the linear conductors 301 based on the configuration of the RF coil unit 310, but the number of the linear conductors 301 and the arrangement thereof are not limited to this example as described above. The number of the linear conductors 301 may be 2N, and it is only required that these 2N linear conductors 301 are arranged at the positions symmetrical with respect to the x-axis 201 and the y-axis 202.

The capacitors may be arranged not only on either of the arcuate conductors 303 and the linear conductors 301, but also on both. For this case, the capacitors are arranged in the arcuate conductors 303 and linear conductors 301, respectively one by one, and the capacitance thereof is assumed as identical in the arcuate conductors 303 or in the linear conductors 301. In other words, the capacitance is identical for each type of the conductors on which the capacitors are arranged. Then, the capacitor is adjusted in such a manner that the RF coil unit becomes the resonant state at the magnetic resonance frequency ($f_c$) that is used in the transceive RF coil 105. The configuration of the RF coil unit may be any of the RF coil units 310, 320, 330, and 340 as described above. Here, an explanation will be made, taking the RF coil unit 310, as an example.

By way of example, the capacitor arranged on the arcuate conductor 303 is assumed as the first capacitor 306, and the capacitor arranged on the linear conductor 301 is assumed as the second capacitor. In addition, capacitance of the first capacitor is assumed as C, and a value of the second capacitor is assumed as $C_2$. Similar to the first capacitor 306, the second capacitor may also be made up of plural capacitors. On this occasion, the combined capacitance of those capacitors is assumed as the capacitance of the second capacitor.

It is to be noted that the inductance $L^l_k{}'$ of the linear conductor 301 provided with the second capacitor is expressed by the formula (53):

[Formula 53]

$$L^{l\prime}_k = L^l_k - \frac{1}{\omega^2 C_2} \quad (53)$$

Therefore, $L^l_k{}'$ is used instead of $L^l_k$ of the equivalent circuit 410 as shown in FIG. 5, thereby obtaining a value of the electrical phase difference $\Delta\theta_k$ (k=1, 2, . . . , N+1). By determining the electrical phase difference $\Delta\theta_k$ (k=1, 2, . . . , N+1) of each loop 309 as described above, each value of the first capacitor 306 and the second capacitor may be configured as constant, irrespective of the locations thereof.

In the present embodiment, an explanation has been made taking an example that the RF coil unit 310 is provided with two feeding ports (the first feeding port 304 and the second feeding port 305). However, the RF coil unit 310 may be provided with four feeding ports (the first feeding port 304, the second feeding port 305, the third feeding port, and the fourth feeding port).

On this occasion, the third feeding port is arranged on the first capacitor 306 at the position being point-symmetrical with the first feeding port 304, with respect to the central axis 311, and the fourth feeding port is arranged on the first capacitor 306 at the position being point-symmetrical with the second feeding port 305 with respect to the central axis 311. Therefore, the four feeding ports are arranged at the positions in such a manner that when power is fed to one feeding port, the amplitude of the RF current flowing on the other feeding port is minimized, on the two feeding ports being adjacent in the circumferential direction of the elliptical loop conductor 132.

The first feeding port 304 and the third feeding port are connected to a high-frequency combiner via a coaxial cable, and further connected to the QD hybrid. The second feeding port 305 and the fourth feeding port are connected to the high-frequency combiner via a coaxial cable and further connected to the QD hybrid. In addition, phase shift circuits for shifting the phase of signal by 180 degrees are inserted respectively between the third feeding port and the high-frequency combiner, and between the fourth feeding port and the high-frequency combiner. Accordingly, the phase difference becomes 180 degrees between the first feeding port 304 and the third feeding port, and RF signals in the same phase are supplied to the coil from the first feeding port 304 and the third feeding port. The phase difference becomes 180 degrees also between the second feeding port 305 and the fourth feeding port, and RF signals in the same phase are supplied to the coil from the second feeding port 305 and the fourth feeding port. Therefore, the resonant state of the RF coil unit 310 becomes the same as in the case where there are two feeding ports. Accordingly, even in the case where there are four feeding ports, the RF coil unit 310 becomes the resonant state at the magnetic resonance frequency ($f_c$), and resonance occurs in the resonant mode where the sensitivity distribution of the coil is homogeneous.

As described above, the RF coil unit (RF coil unit 310, 320, 330, or 340) of the present embodiment is provided with plural linear conductors 301 arranged in parallel with the central axis 311 of the elliptic cylindrical curved surface, along the elliptic cylindrical curved surface, two elliptical loop conductors 302 arranged along the elliptic cylindrical curved surface, in such a manner that loop surfaces thereof are parallel to each other using a point on the central axis 311 as the central point, and plural first capacitors 306, each being made up of at least one capacitor, both ends of each of the linear conductors 301 being connected to the elliptical loop conductor 302, the first capacitors 306 being arranged one by one either respectively on the linear conductors 301, or on an arcuate conductors 303 of the elliptical loop conductor 302, the arcuate conductor being placed between the connection points 308 of the adjacent linear conductors 301, and the plural linear conductors 301 being arranged at the positions line-symmetrical with respect to the major axis and the minor axis of the elliptical loop conductor 302, and the capacitance of the first capacitor 306 being an identical value. On this occasion, the electrical phase difference between the adjacent two arcuate conductors 303 may be determined in such a manner that it increases along with away from the minor axis toward the major axis of the elliptical loop conductor 302, and the electrical phase difference between two arcuate conductors 303 positioned point-symmetrically with respect to the center of the elliptical loop conductor 302 becomes 180 degrees.

In addition, the RF coil unit of the present embodiment (RF coil unit 310, 320, 330, or 340) may be provided with plural second capacitors, each made up of at least one capacitor. On this occasion, the plural second capacitors are arranged one by one respectively on the conductors where the first capacitors 306 are not arranged, either on the linear conductors 301 or on the arcuate conductors 303, and the capacitance of the second capacitor is assumed as identical. In addition, the RF coil unit of the present embodiment (RF coil unit 310, 320, 330, or 340) may be configured in such a manner that distance between the centers of two adjacent linear conductors 301 increases along with away from the minor axis toward the major axis of the elliptical loop conductor 302. Alternatively, the RF coil unit of the present embodiment (RF coil unit 310, 320, 330, or 340) may be configured in such a manner that the width of the linear conductor 301 increase along with away from the minor axis toward the major axis of the elliptical loop conductor 302.

Furthermore, the RF coil unit of the present embodiment (RF coil unit 310, 320, 330, or 340) may be provided with two or four feeding ports 304 and 305 for feeding RF signals to the RF coil unit (RF coil unit 310, 320, 330, or 340). On this occasion, the feeding ports 304 and 305 are arranged at the positions line-symmetrical with respect to either one of the major axis and the minor axis of the elliptical loop conductor 302, and further they are positioned in such a manner that when power is fed to one feeding port, the amplitude of the RF current flowing in the other feeding port is minimized in the two feeding ports 304 and 305 being adjacent in circumferential direction of the elliptical loop conductor 302.

The magnetic resonance imaging apparatus (MRI apparatus 100) of the present embodiment is provided with a static magnetic field generator (magnet 101) for generating a static magnetic field, a gradient magnetic field applying device (gradient magnetic field coil 102) for applying a gradient magnetic field, an RF magnetic field signal generator (transmit RF coil 103) for generating an RF magnetic field signal, a transceive coil (transceive RF coil 105) for irradiating a test subject with the RF magnetic field signal inputted from the RF magnetic field signal generator (RF magnetic field generator 113) and detecting a magnetic resonance signal generated from the test subject to output the signal as a detection signal, a signal processor (computer 120) for subjecting the detection signal to signal processing, and a controller (computer 120) for controlling operations of the gradient magnetic field applying device, the RF magnetic field signal generator, and the signal processor, and the apparatus employs the RF coil unit (any one of the RF coil units 310, 320, 330, and 340) described above, as the transceive coil (transceive RF coil 105).

Second Embodiment

Next, a second embodiment to which the present invention is applied will be explained. The MRI apparatus according to the present embodiment is basically the same as that of the first embodiment. In the first embodiment, the transceive RF coil is used for transmitting an RF magnetic field and receiving a magnetic resonance signal. On the other hand, in the present embodiment, there are provided separately, a transmit RF coil for transmitting the RF magnetic field and a receive RF coil for receiving the magnetic resonance signal. Hereinafter, an explanation will be made as to the present embodiment, focusing on the configuration being different from the first embodiment. It is to be noted that the present embodiment also uses the coordinate system 200 in which the orientation of the static magnetic field 140 generated by the magnet 101 of the horizontal magnetic field system is assumed as the z-axis direction.

Figure 13:
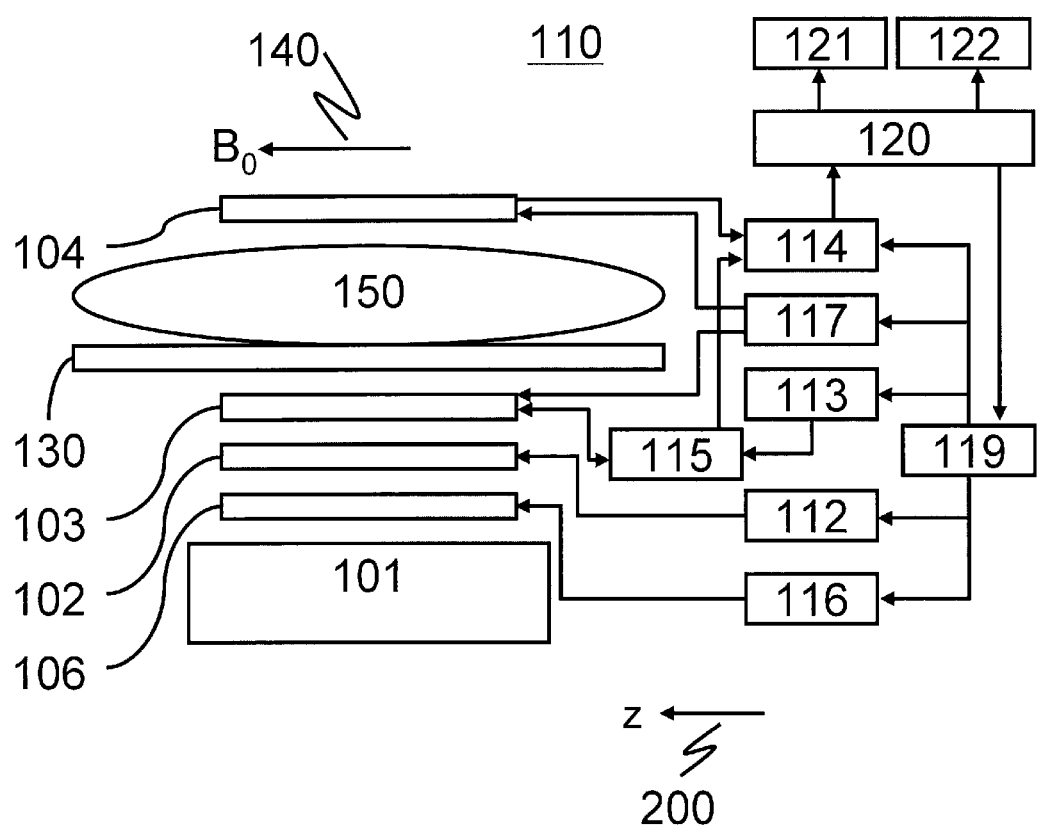
FIG. 13 is a block diagram showing a schematic configuration of the MRI apparatus according to the second embodiment.

FIG. 13 illustrates a block diagram showing a schematic configuration of the MRI apparatus 110 according to the present embodiment. The MRI apparatus 110 of the present embodiment is provided with a magnet 101 of the horizontal magnetic field system, a gradient magnetic field coil 102, a shim coil 106 for adjusting static magnetic field homogeneity, a sequencer 119, a transmit RF coil 103 for generating an RF magnetic field, a receive RF coil 104 arranged near a test subject 150 for receiving an RF signal generated from the test subject 150, a power supply for gradient magnetic field 112, a power supply for shim coil 116, a transmit/receive switching unit 115, an RF magnetic field generator 113, a receiver 114, a magnetic decoupling circuit drive 117, a storage medium 122, a computer 120, a display unit 121, and a table 130.

The gradient magnetic field coil 102 and the shim coil 106 are connected to the power supply for gradient magnetic field 112 and to the power supply for shim coil 116, respectively. The transmit RF coil 103 is connected to the transmit/receive switching unit 115, and the transmit/receive switching unit 115 is connected to the RF magnetic field generator 113 and to the receiver 114. The receive RF coil 104 is connected to the receiver 114.

The magnetic decoupling circuit drive 117 prevents magnetic coupling between the transmit RF coil 103 and the receive RF coil 104. The magnetic decoupling circuit drive 117 is connected to the transmit RF coil 103 and to the receive RF coil 104, and outputs to each of the coils a magnetic coupling prevention signal for switching between operating/non-operating as to both coils, according to an instruction from the sequencer 119.

The magnetic decoupling circuit drive 117 transmits a magnetic coupling prevention signal to the receive RF coil 104, upon applying an RF magnetic field to the test subject 150 via the transmit RF coil 103. Upon receiving the magnetic coupling prevention signal, the receive RF coil 104 becomes open-state, that is, non-operating state. Accordingly, it is possible to avoid magnetic coupling with the transmit RF coil 103.

In addition, the magnetic decoupling circuit drive 117 transmits a magnetic coupling prevention signal to the transmit RF coil 103, when the receive RF coil 104 receives a magnetic resonance signal (RF signal) generated from the test subject 150. Upon receiving the magnetic coupling prevention signal, the transmit RF coil 103 becomes open-state, that is, non-operating state. Accordingly, it is possible to avoid magnetic coupling with the receive RF coil 104.

Other configurations and operations of the MRI apparatus 110 according to the present embodiment are the same as those of the MRI apparatus according to the first embodiment.

Next, an explanation will be made as to the transmit RF coil 103 and the receive RF coil 104 according to the present embodiment.

Firstly, the transmit RF coil 103 of the present embodiment will be explained. Here, an explanation will be made, taking the RF coil unit 350 shown in FIG. 14A and FIG. 14B as an example, being employed as the transmit RF coil 103.

Figure 14A:
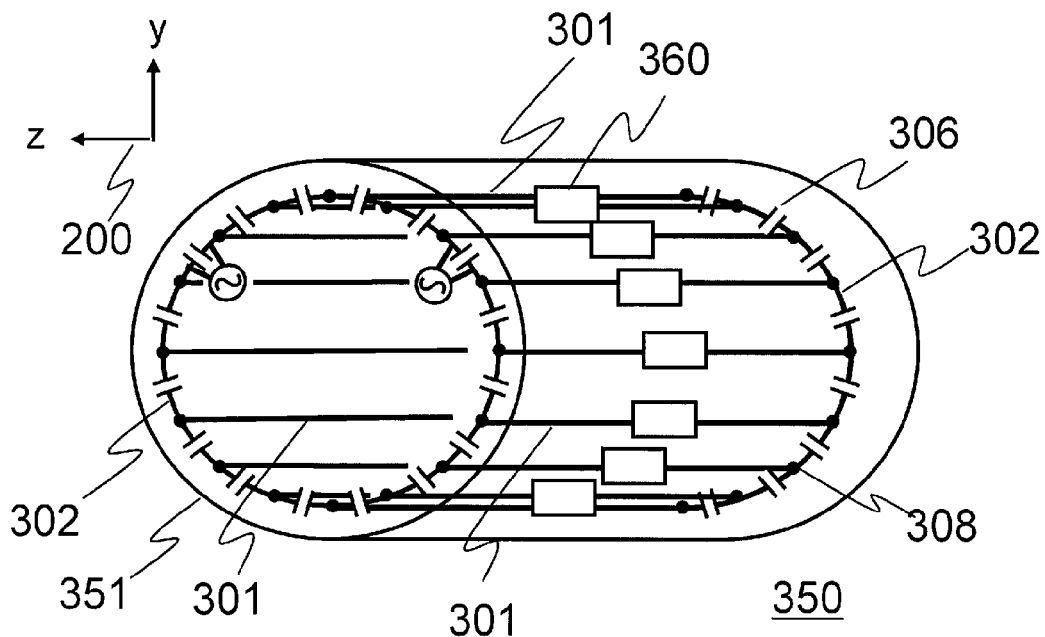
FIG. 14A illustrates the RF coil unit according to the second embodiment.
Figure 14B:
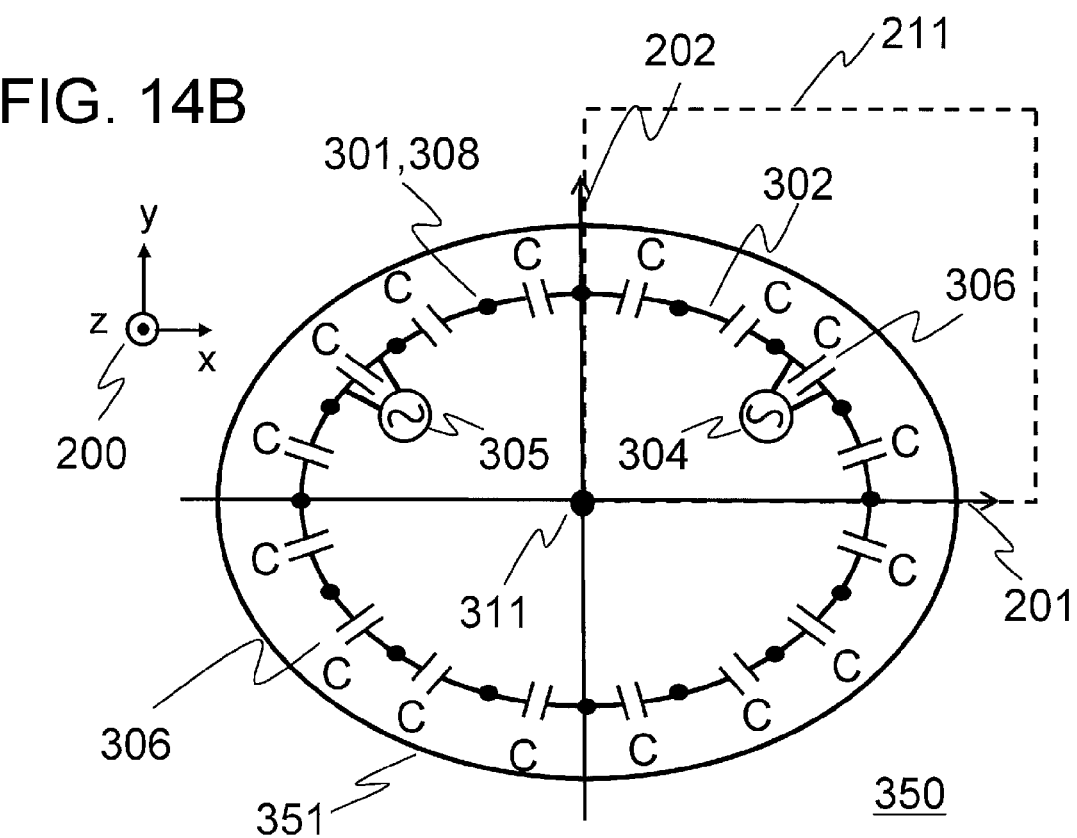
FIG. 14B illustrates the RF coil unit according to the second embodiment.

FIG. 14A is a perspective view of the RF coil unit 350, FIG. 14B illustrates the RF coil unit 350 viewed from the direction of the central axis 311. As illustrated in the figures, the RF coil unit 350 of the present embodiment has basically the same configuration as that of the RF coil unit 310 according to the first embodiment. The RF coil unit 350 of the present embodiment is further provided with an elliptic cylindrical RF shield 351, and a magnetic decoupling circuit 360. The magnetic decoupling circuit 360 is inserted into the linear conductor 301.

Similar to the RF coil unit 310, the RF coil unit 350 is arranged in such a manner that the central axis 311 is along the z-axis direction, the major axis direction of the elliptical loop conductor 302 is along the direction of the x-axis 201, and the minor axis direction is along the direction of the y-axis 202.

The elliptic cylindrical RF shield 351 is arranged outside the elliptical loop conductor 302, sharing the central axis 311, in such a manner that the distance between the elliptical loop conductor 302 and the elliptic cylindrical RF shield 351 becomes constant with respect to the circumferential direction of the elliptical loop conductor 302. Here, the distance between the elliptical loop conductor 302 and the elliptic cylindrical RF shield 351 is assumed as $d_g$.

Also in the present embodiment, the RF coil unit 350 becomes the resonant state at a magnetic resonance frequency ($f_c$) according to plural first capacitors 360 having identical capacitance, and resonance occurs in the resonant mode where the sensitivity distribution of the coil is homogeneous. Therefore, similar to the RF coil unit 310 of the first embodiment, N−1 linear conductors 301 being placed in the first quadrant 211, out of 4N linear conductors 301, are arranged in such a manner that the connection points of the N−1 linear conductors satisfy the aforementioned formula (1). The linear conductors 301 in the other quadrants are arranged at the positions line-symmetrical with respect to the y-axis 202 and the x-axis 201.

On this occasion, the electrical phase difference $\Delta\theta_k$ between each of the loops 309 is adjusted so that it satisfies the formula (2), the formula (3), the formula (4), the formula (5), and the formula (6).

It is to be noted that in the RF coil unit 350, values of self inductance $L^{ls}_k$ of the linear conductor 301 and equivalent inductance $L^r_k$ of the arcuate conductor 303 are changed by the elliptic cylindrical RF shield 351.

Since the linear conductor 301 may be assumed as a microstripline, when one of approximate expressions used for calculating inductance of the microstripline is employed, the self inductance $L^{lss}_k$ of the linear conductor 301 under the condition that the elliptic cylindrical RF shield 351 is arranged, is expressed by the following formula (54) and formula (55):

[Formula 54]

$$L^{lss}_k = \frac{l}{2\pi\varepsilon_0}\log\left(\frac{8d_g}{w_k} + \frac{w_k}{4d_g}\right)(w_k \leq d_g) \quad (54)$$

[Formula 55]

$$L^{lss}_k = \frac{l}{\varepsilon_0}\left[\frac{w_k}{d_g} + 1.393 + 0.667\cdot\log\left(\frac{w_k}{d_g} + 1.444\right)\right]^{-1}(w_k > d_g) \quad (55)$$

Here, $w_k$ is assumed as the width of the linear conductor 301, and l is assumed as the length of the linear conductor 301.

Similarly, the equivalent inductance $L^{rs}_k$ of the arcuate conductor 303 under the condition that the elliptic cylindrical RF shield 351 is arranged, is expressed by the following formula (56) or formula (57):

[Formula 56]

$$L^{rs}_k = \frac{l^r_k}{2\pi\varepsilon_0}\log\left(\frac{8d_g}{w^r} + \frac{w^r}{4d_g}\right)(w^r \leq d_g) \quad (56)$$

[Formula 57]

$$L^{rs}_k = \frac{l^r_k}{\varepsilon_0}\left[\frac{w^r}{d_g} + 1.393 + 0.667\cdot\log\left(\frac{w^r}{d_g} + 1.444\right)\right]^{-1}(w^r > d_g) \quad (57)$$

Here, $w_r$ represents the width of the arcuate conductor 303, and $l^r_k$ represents the length of the arcuate conductor 303.

A value of each electrical phase difference $\Delta\theta_k$ (k=1, 2, ..., N+1) can be obtained by solving the formula (2), the formula (3), the formula (4), the formula (5), and the formula (6). On this occasion, $L^{lss}{}_k$ instead of the self inductance $L^{ls}{}_k$ of the linear conductor 301, and $L^{rs}{}_k$ instead of the equivalent inductance $L^r{}_k$ of the arcuate conductor 303 are used respectively, and then the formula (5) and the formula (6) are solved.

In order to satisfy the formula (4) similar to the RF coil unit 310, also in the coil unit 350 of the present embodiment, the linear conductors 301 are arranged at the positions, with the change of the electrical phase difference by 360 degrees, after going round along the elliptical loop conductor 302. Therefore, the RF coil unit 350 becomes the resonant state at the magnetic resonance frequency ($f_c$), and resonance occurs in the resonant mode where the sensitivity distribution of the coil is homogeneous.

Therefore, the RF coil unit 350 of the present embodiment becomes the resonant state at the magnetic resonance frequency ($f_c$) according to plural first capacitors 306 having an identical capacitance, and resonance occurs in the resonant mode where the sensitivity distribution of the coil is homogeneous.

Figure 15A:
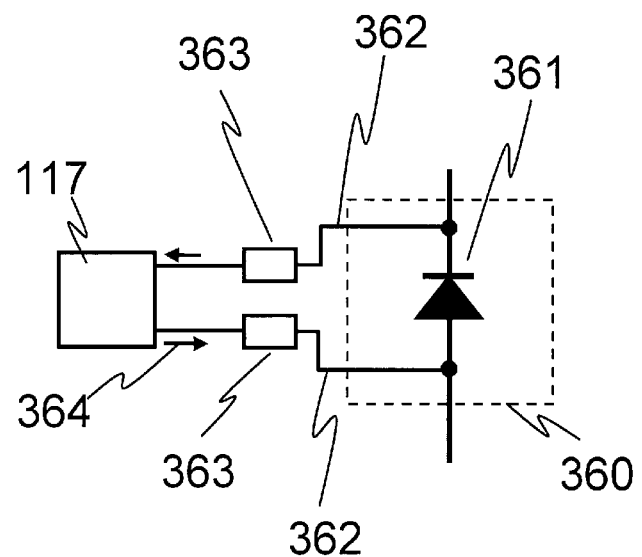
FIG. 15A illustrates a magnetic decoupling circuit of the RF coil unit according to the second embodiment.
Figure 15B:
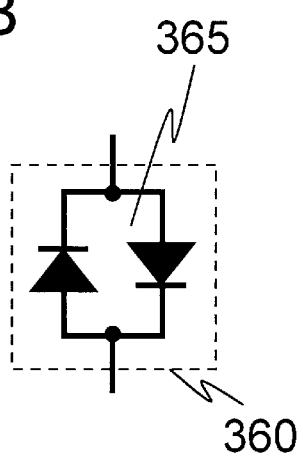
FIG. 15B illustrates a magnetic decoupling circuit of the RF coil unit according to the second embodiment.

Next, an explanation will be made as to the magnetic decoupling circuit 360 that is inserted into the RF coil unit 350. FIG. 15A and FIG. 15B illustrate details of the magnetic decoupling circuit 360 that is inserted into the RF coil unit 350.

As shown in FIG. 15A, the magnetic decoupling circuit 360 is provided with the PIN diode 361, and the control line 362 being connected to both ends of the PIN diode 361. The PIN diode 361 has a property to become almost conductive, when a value of DC current flowing in the forward direction of the diode is equal to or higher than a certain value, and the DC current performs ON/OFF control.

The PIN diode 361 is connected to the output terminal of the magnetic decoupling circuit drive 117, via the control lines 362 connected to both ends of the diode, respectively, passing through the choke coils 363 for insulating an RF signal electrically. Control current 364 from the magnetic decoupling circuit drive 117 performs ON/OFF control on the PIN diode 361, and the magnetic decoupling circuit 360 allows the RF coil unit 350 to function as the transmit RF coil upon irradiation of an RF magnetic field, whereas upon receiving an RF signal, the magnetic decoupling circuit 360 changes the RF coil unit 350 to have high impedance, thereby preventing interference with the receive RF coil. Details of the operation will be described below.

Figure 16A:
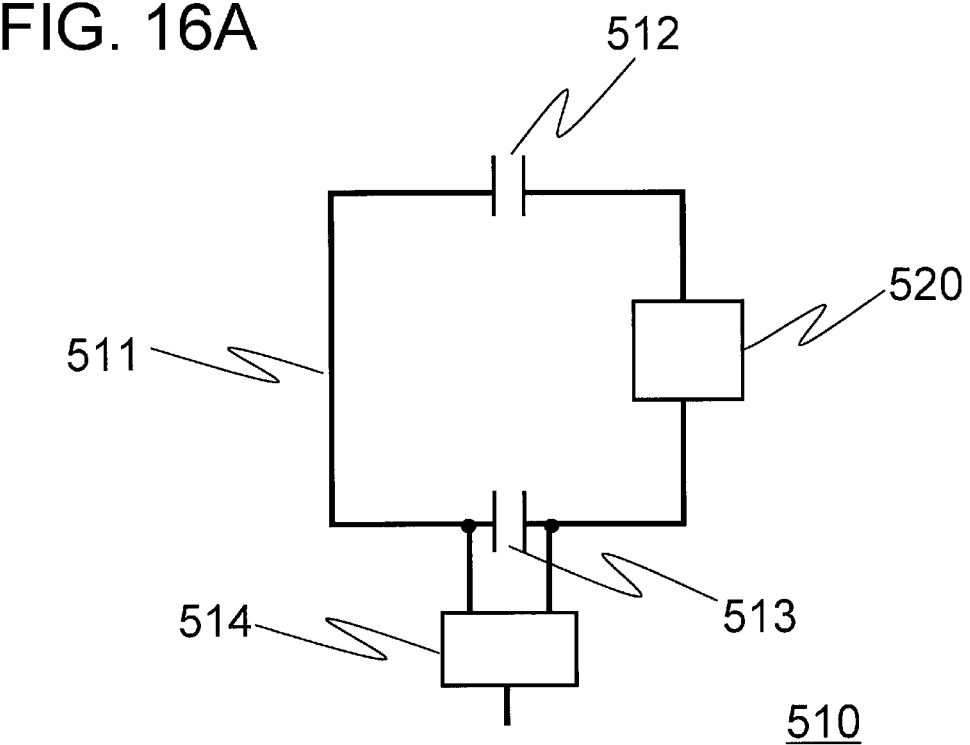
FIG. 16A illustrates a surface coil of the second embodiment.
Figure 16B:
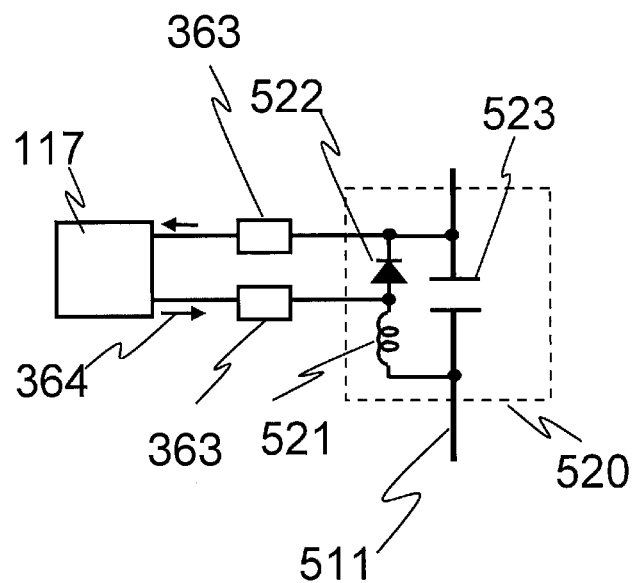
FIG. 16B illustrates the magnetic decoupling circuit in the surface coil of the second embodiment.

Next, the receive RF coil 104 of the present embodiment will be explained. In the present embodiment, an explanation will be made, taking as an example a surface coil 510 as shown in FIG. 16A and FIG. 16B, being employed as the receive RF coil 104. FIG. 16A illustrates a configuration of the surface coil 510, and FIG. 16B illustrates details of the magnetic decoupling circuit 520 inserted into the surface coil 510 and a relation of connection with the magnetic decoupling circuit drove unit 117.

As shown in FIG. 16A, the surface coil 510 is provided with a loop conductor 511, a capacitor 512, a matching capacitor 513, a magnetic decoupling circuit 520, and a balun 514 for removing a common mode noise. The capacitor 512, the matching capacitor 513, and the magnetic decoupling circuit 520 are inserted into the loop conductor 511. The balun 514 is connected to the loop conductor 511, via wiring provided on both ends of the matching capacitor 513. The output from the balun 514 is connected to the preamplifier (not illustrated), and it is further connected to the receiver 114 via the coaxial cable.

As shown in FIG. 16B, the magnetic decoupling circuit 520 is provided with a circuit where the inductor 521 and the PIN diode 522 are connected in series, and the capacitor 523 connected in parallel with the circuit. The PIN diode 522 has a property to become almost conductive state when a value of the DC current in the forward direction of diode is equal to or higher than a certain value, and the DC current performs ON/OFF control.

Both ends of the PIN diode 522 are respectively connected to the output terminals of the magnetic decoupling circuit drive 117 passing through the choke coils 363. The control current 364 from the magnetic decoupling circuit drive 117 performs ON/OFF control on the PIN diode 522, and upon receiving an RF signal, the PIN diode allows the surface coil 510 to function as the receive RF coil, whereas upon transmitting an RF magnetic field, the surface coil 510 is allowed to have high impedance, thereby performing control so as not to interfere with the transmit RF coil 103. Those operations will be described in detail later.

The capacitor 512, the capacitor 523, and the matching capacitor 513 are adjusted in such a manner that the surface coil 510 resonates at the magnetic resonance frequency that is set in the MRI apparatus 110 of the present embodiment, and an impedance of the coil viewed from both ends of the matching capacitor 513 becomes a predetermined value. The magnetic decoupling circuit 520 is adjusted in such a manner that when the PIN diode 522 is in the ON state, the inductor 521 and the capacitor 523 resonate at the magnetic resonance frequency that is set in the MRI apparatus 110.

Next, with reference to FIG. 13 to FIG. 16B, an explanation will be made as to the RF coil unit 350 operating as the transmit RF coil 103, and the surface coil 510 operating as the receive RF coil 104.

Firstly, immediately before applying an RF signal for irradiation of RF magnetic field from the RF magnetic field generator 113, the magnetic decoupling circuit drive 117 applies DC control current 364, so that the PIN diode 361 of the magnetic decoupling circuit 360 in the RF coil unit 350, and the PIN diode 522 of the magnetic decoupling circuit 520 in the surface coil 510 become ON state.

In the RF coil unit 350, the control current 364 flowing in the PIN diodes 361 turns on all the PIN diodes 361. When all the PIN diodes 361 in the RF coil unit 350 are in the ON state, the PIN diodes 361 become conductive, thereby rendering the RF coil unit 350 operable. On this occasion, similar to the case of the RF coil unit 310 shown in FIG. 3A and FIG. 3B, the RF coil unit 350 resonates at the resonant mode where the sensitivity distribution of the coil is homogeneous.

On the other hand, in the surface coil 510, the control current 364 turns on the PIN diode 522, and the magnetic decoupling circuit 520 serves as a parallel resonant circuit that incorporates the inductor 521 and the capacitor 523. Impedance of this parallel resonant circuit becomes high at the magnetic resonance frequency that is set in the MRI apparatus 110, and the loop conductor 511 of the surface coil 510 becomes almost open state. As a result, the surface coil 510 does not resonate at the magnetic resonance frequency set in the MRI apparatus 110, and almost no current flows in the loop conductor 511. Therefore, no magnetic coupling occurs between the RF coil unit 350 and the surface coil 510, and the RF coil unit 350 is allowed to irradiate the test subject 150 with the RF magnetic field, without shifting of resonance frequency nor reducing the Q-value of the coil that are caused by the magnetic coupling.

After applying the control current 364 by the magnetic decoupling circuit drive 117, the RF magnetic field generator 113 applies an RF signal. On this occasion, the transmit/receive switching unit 115 is switched so that the RF signal is transferred to the transmit RF coil 103, and the RF signal is inputted into each of the first feeding port 304 and the second feeding port 305.

In the case where all the PIN diode 361 are in the ON state, the RF coil unit 350 operates in the same manner as in the case of the RF coil unit 310, and the RF coil unit 350 irradiates the test subject 150 with the RF magnetic field, similar to the first embodiment, in the same manner as the QD irradiation method for performing irradiation by shifting one phase of the two-way RF magnetic fields being orthogonal to each other by 90 degrees.

After irradiation of the RF magnetic field, in order to receive a magnetic resonance signal emitted from the test subject 150, the magnetic decoupling circuit drive 117 sets the value of the control current 364 to be zero, so as to turning off the PIN diode 361 in the magnetic decoupling circuit 360 in the RF coil unit 350, and the PIN diode 522 in the magnetic decoupling circuit 520 in the surface coil 510.

When the value of the control current 364 becomes zero, the PIN diodes 361 in the RF coil unit 350 are turned off, bringing about highly resistive state. Consequently, almost no current flows in the conductors of the RF coil unit 350, and the RF coil unit 350 does not resonate at the magnetic resonance frequency set in the MRI apparatus 110, nor almost no magnetic field is generated. On the other hand, in the surface coil 510, the PIN diode 522 is turned off, and the magnetic decoupling circuit 520 operates as the capacitor 523. As a result, the surface coil 510 resonates at the magnetic resonance frequency set in the MRI apparatus 110.

Therefore, upon receiving the magnetic resonance signal emitted from the test subject 150, there is no more magnetic coupling between the surface coil 510 and the RF coil unit 350, and the surface coil 510 is allowed to receive the magnetic resonance signal with high sensitivity, without shifting of resonance frequency nor reducing of the Q-value of the coil that are caused by the magnetic coupling. The signal received by the surface coil 510 is amplified by the preamplifier and transferred to the receiver 114.

As described above, the RF coil unit 350 as shown in FIG. 11A and FIG. 11B operates as the transmit RF coil 103, and the surface coil 510 as shown in FIG. 13 operates as the receive RF coil 104.

As described above, according to the present embodiment, it is possible to provide an elliptical birdcage coil allowing that, the impedance in the surface coil 510 is raised to be high upon applying the RF magnetic field, and the impedance in the RF coil unit 350 is raised to be high upon receiving the magnetic resonance signal, thereby preventing magnetic coupling between the transmit RF coil 103 and the receive RF coil 104 in which resonance occurs at the magnetic resonance frequency, and the elliptical birdcage coil serving as the transmit RF coil 103 achieving an identical capacitance. This allows reduction of trouble and effort upon manufacturing, production cost, and a swell of variations in coil performance of the elliptical birdcage coil.

Figure 17A:
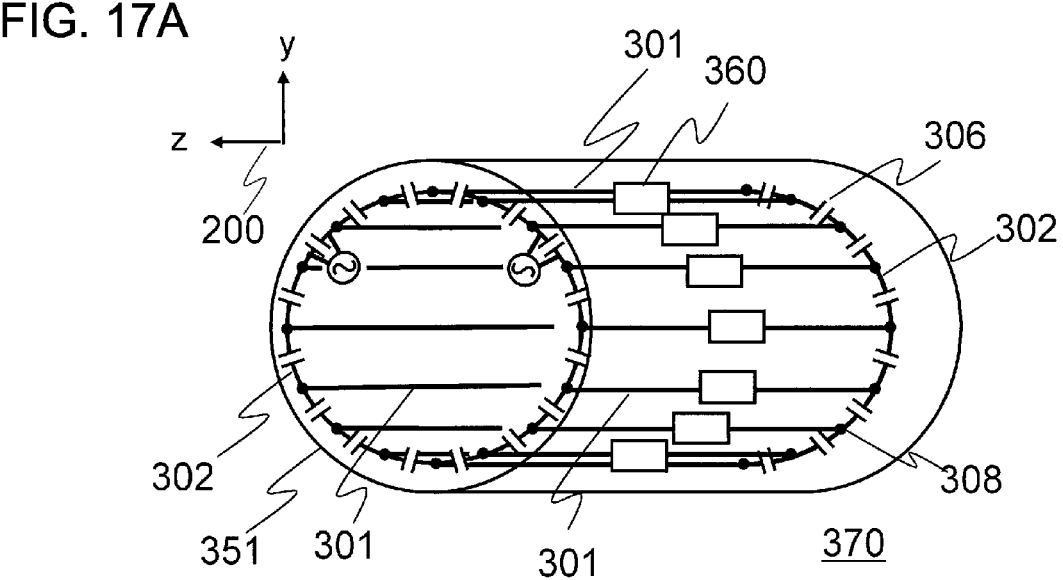
FIG. 17A illustrates a modification example of the RF coil unit according to the second embodiment.
Figure 17B:
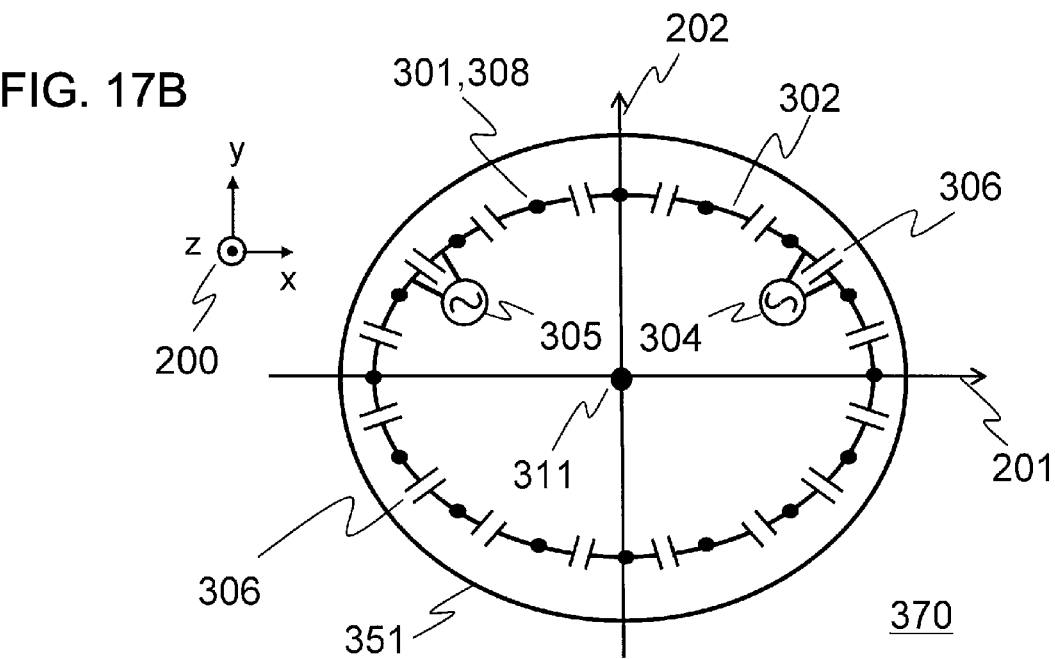
FIG. 17B illustrates a modification example of the RF coil unit according to the second embodiment.
Figure 18A:
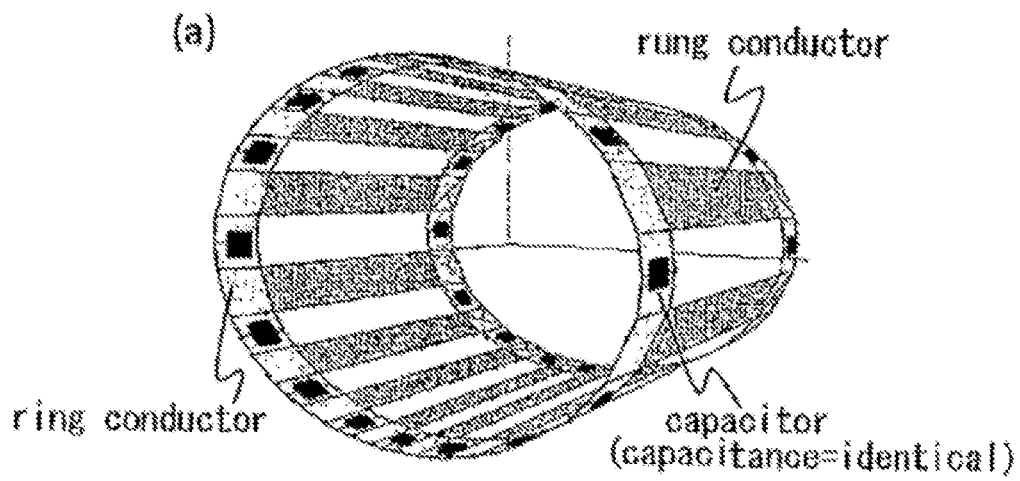
FIG. 18A illustrates a perspective view of an Elliptical birdcage coil with capacitors having the same capacitance.
Figure 18B:
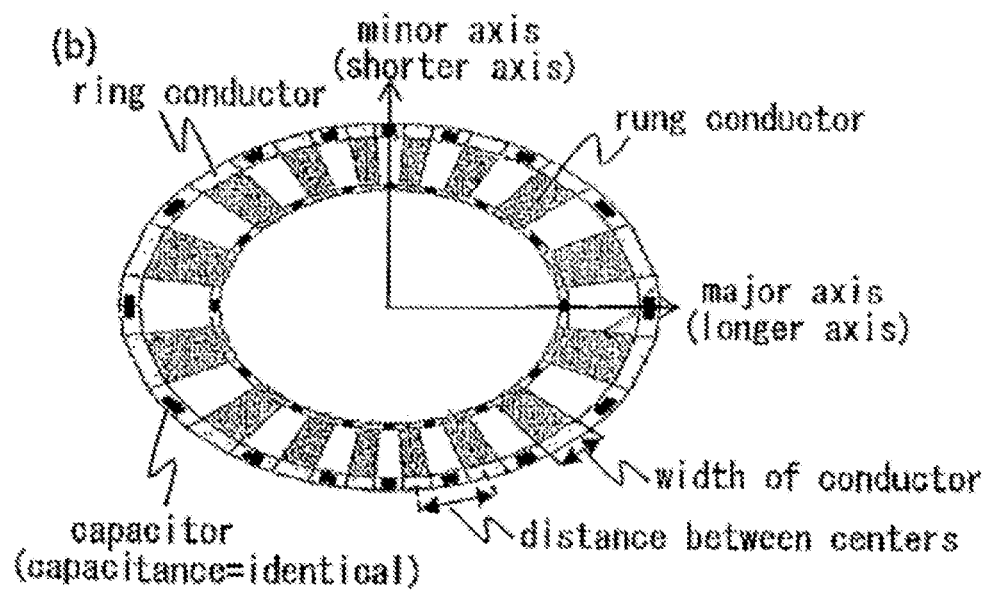
FIG. 18B illustrates a front view of an Elliptical birdcage coil with capacitors having the same capacitance.

It is to be noted that the shape of the elliptic cylindrical RF shield 351 is not limited to the aforementioned example. By way of example, a different shape may be applicable, such as having distance between the elliptic cylindrical RF shield 351 and the elliptical loop conductor 302, the distance becoming shorter along with going away from an intersection point with the y-axis 202 toward an intersection point with the x-axis 201. FIG. 17A and FIG. 17B illustrate an example of the RF coil unit 370 for the case above.

Also for this case, similar to the aforementioned RF coil unit 350, the electrical phase difference $\Delta\theta_k$ between each of the loops is adjusted in such a manner as satisfying the formula (2), the formula (3), the formula (4), the formula (5) and the formula (6).

As shown in FIG. 17B, when it is assumed that the distance between the k-th linear conductor 301 counting from the y-axis 202 in the circumferential direction of the elliptical loop conductor 302 in clockwise, and the elliptic cylindrical RF shield 351 is $d^l_k$; and in the first quadrant 211 as shown in FIG. 17B, when it is assumed that average distance between the k-th arcuate conductor 303 counting from the y-axis 202 in the circumferential direction of the elliptical loop conductor 302 in clockwise and the elliptic cylindrical RF shield 351 is $d^r_k$, the self-inductance $L^{lss}_k$ of the linear conductor 301 when the elliptic cylindrical RF shield 351 is arranged, is expressed by the formula (58) or the formula (59):

[Formula 58]

$$L^{lss}_k = \frac{l}{2\pi\varepsilon_0}\log\left(\frac{8d^l_k}{w_k} + \frac{w_k}{4d^l_k}\right)(w_k \leq d^l_k) \quad (58)$$

[Formula 59]

$$L^{lss}_k = \frac{l}{\varepsilon_0}\left[\frac{w_k}{d^l_k} + 1.393 + 0.667\cdot\log\left(\frac{w_k}{d^l_k} + 1.444\right)\right]^{-1}(w_k > d^l_k) \quad (59)$$

Here, the width of the linear conductor 301 is represented as $w_k$, and the length of the linear conductor 301 is represented as l.

Similarly, as for the equivalent inductance $L^r_k$ of the arcuate conductor 303, the equivalent inductance of the arcuate conductor 303 when the elliptic cylindrical RF shield 351 is arranged is expressed by the formula (60), or the formula (61):

[Formula 60]

$$L^{rs}_k = \frac{l^r_k}{2\pi\varepsilon_0}\log\left(\frac{8d^r_k}{w^r} + \frac{w^r}{4d^r_k}\right)(w^r \leq d^r_k) \quad (60)$$

[Formula 61]

$$L^{rs}_k = \frac{l^r_k}{\varepsilon_0}\left[\frac{w^r}{d^r_k} + 1.393 + 0.667\cdot\log\left(\frac{w^r}{d^r_k} + 1.444\right)\right]^{-1}(w^r > d^r_k) \quad (61)$$

Here, the width of the arcuate conductor 303 is represented by $w_r$, and the length of the arcuate conductor 303 is represented by $l^r_k$.

A value of each electrical phase difference $\Delta\theta_k$ (k=1, 2, ..., N+1) can be obtained by solving the formula (2), the formula (3), the formula (4), the formula (5), and the formula (6). On this occasion, $L^{lss}_k$ is used instead of the self inductance $L^{ls}_k$ of the linear conductor 301, and $L^{rs}_k$ is used instead of the equivalent inductance $L^r_k$ of the arcuate conductor 303, and then the formula (5) and the formula (6) are solved.

It is to be noted that the RF coil unit 350 is provided with 4N linear conductors 301, and four linear conductors 301 among them are arranged on the x-axis 201 and the y-axis 202. However, this is not the only arrangement for the linear conductor 301. Similar to the first embodiment, it is only required that 4N linear conductors are arranged at the positions symmetrical with respect to the x-axis 201 and the y-axis 202. In addition, the number of the linear conductors 301 is not limited to this example. Similar to the first embodiment, the number may be 2N, being arranged at the positions symmetrical with respect to the x-axis 201 and the y-axis 202.

In the RF coil unit 350, the magnetic decoupling circuit 360 employs the PIN diode 361, but instead of the PIN diode 361, it is possible to employ the cross diode 365 as shown in FIG. 15B. On this occasion, it is not necessary to provide the magnetic decoupling circuit drive 117.

The cross diode 365 is turned on by the RF signal applied to the RF coil unit 350, and it is rendered conductive state. If the RF signal is not applied any more, it is turned off, resulting in highly resistive state. This operation is the same as that of the PIN diode 361, and by using the cross diode 365, the RF coil unit 350 operates as the transmit RF coil 103, without generating magnetic coupling with the surface coil 510, even though there is no control by the magnetic decoupling circuit drive 117.

Similar to the first embodiment, also in the RF coil unit 350, a second capacitor may be inserted into the linear conduct 301, in addition to the first capacitor 306 that is inserted into the arcuate conductor 303. On this occasion, if a value of the second capacitor is assumed as $C_2$, the inductance $L^I_k{'}$ of the linear conductor 301 including the second capacitor is expressed by the formula (52). Therefore, it is only required to obtain a value of $\Delta\theta_k$ (k=1, 2, . . . , N+1), using $L^I_k{'}$ being substituted for $L^I_k$. Accordingly, it is possible to keep the values of the first capacitor 306 and the second capacitor to be constant, irrespective of their positions.

In the present embodiment, an explanation has been made, taking as an example that the RF coil unit 350 is operated as the transmit RF coil 103 and the surface coil 510 is operated as the receive RF coil 104, but this is not the only example. By way of example, the RF coil unit 350 may be used as both the transmit RF coil 103 and the receive RF coil 104.

An operation in which the transmit RF coil 103 is used for both transmitting and receiving will be described below.

Firstly, immediately before applying an RF signal for irradiation of the RF magnetic field from the RF magnetic field generator 113, the magnetic decoupling circuit drive 117 applies DC control current 364 so that the PIN diode 361 of the RF coil unit 350 and the PIN diode 522 of the surface coil 510 become ON state.

In the RF coil unit 350, the control current 364 flows into the PIN diodes 361, thereby turning on all the PIN diodes 361. When all the PIN diodes 361 in the RF coil unit 350 are turned on, this renders the PIN diodes 361 conductive, and thus the RF coil unit 350 becomes operable. On this occasion, similar to the RF coil unit 310 as shown in FIG. 3A and FIG. 3B, the RF coil unit 350 resonates in the resonant mode where the sensitivity distribution of the coil is homogeneous.

On the other hand, in the surface coil 510, the control current 364 turns on the PIN diode 522, and the magnetic decoupling circuit 520 serves as a parallel resonant circuit incorporating the inductor 521 and the capacitor 523. This parallel resonant circuit has high impedance at the magnetic resonance frequency that is set in the MRI apparatus 110, and the loop conductor 511 of the surface coil 510 becomes almost open state. Consequently, the surface coil 510 does not resonate at the magnetic resonance frequency that is set in the MRI apparatus 110, and almost no current flows in the loop conductor 511. Therefore, no magnetic coupling occurs between the RF coil unit 350 and the surface coil 510, and the RF coil unit 350 irradiates the test subject 150 with the RF magnetic field, without shifting the resonance frequency nor reducing the Q-value that are caused by the magnetic coupling.

After applying the control current 364 by the magnetic decoupling circuit drive 117, the RF magnetic field generator 113 applies RF signals. On this occasion, the transmit/receive switching unit 115 is switched so that the RF signals are transferred to the transmit RF coil 103, and the RF signals are respectively inputted into the first feeding port 304 and the second feeding port 305.

When all the PIN diodes 361 are turned on, the RF coil unit 350 operates in the similar manner as the RF coil unit 310. Therefore, as in the case of the first embodiment, the RF coil unit 350 irradiates the test subject 150 with the RF magnetic field, in the same manner as the QD irradiation method in which one phase of the RF magnetic field out of orthogonal two-way RF magnetic fields is shifted by 90 degrees for irradiation.

After irradiation of the RF magnetic field, the RF coil unit 350 receives the magnetic resonance signal issued from the test subject 150, and therefore, the magnetic decoupling circuit drive 117 sets a value of the control current 364 so that the PIN diode 361 of the RF coil unit 350 and the PIN diode 522 of the surface coil 510 are turned on. In the RF coil unit 350, the control current 364 flowing in the PIN diodes 361 turns on all the PIN diodes 361. When all the PIN diodes 361 of the RF coil unit 350 are turned on, the PIN diodes 361 are rendered conductive, and therefore, the RF coil unit 350 becomes operable. On this occasion, similar to the RF coil unit 310, the RF coil unit 350 resonates in the resonant mode where the sensitivity distribution of the coil is homogeneous.

On the other hand, in the surface coil 510, the control current 364 turns on the PIN diode 522, and the magnetic decoupling circuit 520 serves as the parallel resonant circuit incorporating the inductor 521 and the capacitor 523. This parallel resonant circuit has high impedance at the magnetic resonance frequency that is set in the MRI apparatus 110, and the loop conductor 511 of the surface coil 510 becomes almost open state. Consequently, the surface coil 510 does not resonate at the magnetic resonance frequency set in the MRI apparatus 110, and almost no current flows in the loop conductor 511.

Therefore, upon receiving the magnetic resonance signal issued from the test subject 150, any more magnetic coupling does not occur between the surface coil 510 and the RF coil unit 350, and it is possible for the RF coil unit 350 to receive with high sensitivity, the magnetic resonance signal without shifting of the resonance frequency nor reducing the Q-value that are caused by the magnetic coupling. The transmit/receive switching unit 115 transfers the signal received by the RF coil unit 350 to the receiver 114.

As described above, it is shown that the RF coil unit 350 operates as both the transmit RF coil 103 and the receive RF coil 104.

As discussed above, the RF coil unit (RF coil unit 350) of the present embodiment is provided with plural linear conductors 301 arranged along the elliptic cylindrical curved surface in parallel with the central axis 311 thereof, two elliptical loop conductors 302 that are arranged, setting a point on the central axis 311 as a center, in such a manner that loop surfaces are parallel with each other along the elliptic cylindrical curved surface, and plural first capacitors 306, each made up of at least one capacitor, and both ends of each of the linear conductors 301 being connected to the elliptical loop conductors 302, respectively, the first capacitors 306 being arranged one by one respectively on the linear conductors 301, or the arcuate conductors 303 of the elliptical loop conductor 302, the arcuate conductor being placed between the connection points 308 with the linear conductors 301 being adjacent, and the plural linear conductors 301 being arranged at the positions line-symmetrical with respect to the major axis and the minor axis of the elliptical loop conductor 302, and the capacitance of the first capacitors 306 being an identical value.

In addition, the RF coil unit (RF coil unit 350 or 370) of the present embodiment may be further provided with a cylindrically shaped shield 351 that shares the central axis 311 of the elliptic cylindrical curved surface. On this occasion, the shield 351 may be arranged outside the elliptic cylindrical curved surface. In addition, the shield 351 may have a cylindrical shape that has constant distance between the shield surface and the elliptic cylindrical curved surface. The shield 351 may have a cylindrical shape that the distance between the shield surface and the elliptic cylindrical curved surface becomes shorter along with going away from the minor axis toward the major axis on the cross section that is orthogonal to the central axis 311 of the elliptic cylindrical curved surface.

The RF coil unit (RF coil unit 350 or 370) of the present embodiment may be provided with a magnetic decoupling circuit (magnetic decoupling circuit 360) for preventing mutual magnetic coupling. On this occasion, the magnetic decoupling circuit (magnetic decoupling circuit 360) may be arranged in the linear conductor 301 or in the arcuate conductor 303. The magnetic decoupling circuit (magnetic decoupling circuit 360) may be the PIN diode 361. Alternatively, the magnetic decoupling circuit (magnetic decoupling circuit 360) may be a circuit 520 that is obtained by connecting a circuit in which the PIN diode 522 and the inductor 521 are serially connected, in parallel with the capacitor 523.

The magnetic resonance imaging apparatus (MRI apparatus 100) of the present embodiment is provided with; a static magnetic field generator (magnet 101) for generating a static magnetic field, a gradient magnetic field applying device (gradient magnetic field coil 102) for applying a gradient magnetic field, an RF magnetic field signal generator (transmit RF coil 103) for generating an RF magnetic field signal, a transceive coil (transceive RF coil 105) for irradiating the test subject 150 with the RF magnetic field signal inputted from the RF magnetic field signal generator (RF magnetic field generator 113), detecting a magnetic resonance signal issued from the test subject, and outputting the signal as a detection signal, a signal processor (computer 120) for subjecting the detection signal to a signal processing, and a controller (computer 120) for controlling the operations of the gradient magnetic field applying device, the RF magnetic field signal generator, and the signal processor, and the magnetic resonance imaging apparatus may employ the aforementioned RF coil unit (RF coil unit 350 or 370) as the transceive coil (transceive RF coil 105).

The magnetic resonance imaging apparatus (MRI apparatus 100) of the present embodiment is provided with; a static magnetic field generator (magnet 101) for generating a static magnetic field, a gradient magnetic field applying device (gradient magnetic field coil 102) for applying a gradient magnetic field, an RF magnetic field signal generator (transmit RF coil 103) for generating an RF magnetic field signal, a transmission coil (transmit RF coil 103) for irradiating a test subject 150 with the RF magnetic field signal inputted from the RF magnetic field signal generator, a reception coil (receive RF coil 104) for detecting a magnetic resonance signal issued from the test subject 150 and outputting a detection signal, a signal processor (computer 120) for subjecting the detection signal to a signal processing, a controller (computer 120) for controlling operations of the gradient magnetic field applying device, the RF magnetic field signal generator, and the signal processor, and the magnetic resonance imaging apparatus may employ the aforementioned RF coil unit (RF coil unit 350 or 370) as the transmission coil (transmit RF coil 103).

Therefore, according to the present embodiment, switching the control current of the magnetic decoupling circuit drive 117 allows the RF coil unit 350 to be used only as the transmit RF coil 103, or to be used as both the transmit RF coil 103 and the receive RF coil 104, and this increases the degree of freedom in selecting the reception coil.

Consequently, according to the present embodiment, it is possible to keep the value of the combined capacitance of the capacitors placed on the ring conductors to be constant, irrespective of the positions where they are arranged. In addition, it is possible to keep the value of the combined capacitance of the capacitors placed on the rung conductors to be constant, irrespective of the positions where they are arranged. Accordingly, this allows reduction of trouble and effort upon manufacturing, production cost, and variations in coil performance of the elliptical birdcage coil.

It is to be noted that the RF coil unit 310 of the first embodiment may also be provided with the RF shield 351.

In each of the aforementioned embodiments, the linear conductor 301 and the elliptical loop conductor 302 (arcuate conductor 303) may have a rod-like shape, or a sheet-like shape.

EXPLANATION OF REFERENCES

100: MRI apparatus, 101: magnet, 102: gradient magnetic field coil), 103: transmit RF coil, 104: receive RF coil, 105: transceive RF coil, 106: shim coil, 110: MRI apparatus, 112: power supply for gradient magnetic field, 113: RF magnetic field generator, 114: receiver, 115: transmit-receive switch, 116: power supply for shim coil, 117: magnetic decoupling circuit drive, 119: sequencer, 120: computer, 121: display unit, 122: storage medium, 130: table, 140: static magnetic field), 150: test subject, 200: coordinate system, 201: x-axis, 202: y-axis, 203: z-axis, 211: first quadrant, 301: linear conductor, 302: elliptical loop conductor, 303: arcuate conductor, 304: first feeding port, 305: second feeding port, 306: first capacitor, 308: connection point, 309: loop, 310: RF coil unit, 311: central axis, 312: loop current, 320: RF coil unit, 330: RF coil unit, 340: RF coil unit, 350: RF coil unit, 351: elliptic cylindrical RF shield, 360: magnetic decoupling circuit, 361: PIN diode, 362: control line, 363: choke coil, 364: control signal, 365: cross diode, 370: RF coil unit, 410: equivalent circuit, 411: inductance of arcuate conductor, 412: inductance of linear conductor, 413: virtual ground, 420: equivalent circuit, 430: equivalent circuit, 440: equivalent circuit, 510: surface coil, 511: loop conductor, 512: capacitor, 513: matching capacitor, 514: balun, 520: magnetic decoupling circuit, 906: capacitor, 910: elliptical birdcage coil

What is claimed is:
1. A magnetic resonance imaging apparatus comprising:
a coil, the coil comprising:
two elliptical ring conductors having an arc shape at least partially, the two elliptical ring conductors being arranged in parallel with each other;
a plurality of linear conductors, both ends of each of the plurality of linear conductors being connected to the elliptical ring conductors, respectively; and a plurality of capacitors, each of the plurality of capacitors comprising at least one capacitor, and each of the plurality of capacitors having a substantially identical capacitance, wherein at least one of the plurality of capacitors is arranged one by one on a linear conductor and/or on an arc-shaped conductor, the arc-shaped conductor forming a part of the elliptical ring conductor, and the arc-shaped conductor being placed between connection points of the linear conductors, which are adjacent, wherein the plurality of linear conductors are arranged line symmetrically with respect to a major axis and a minor axis of the elliptical ring conductor, and wherein a width of each of the plurality of linear conductors and a distance between the centers of the adjacent linear conductors increase along with going away from the minor axis toward the major axis of the elliptical ring conductor.

2. The magnetic resonance imaging apparatus according to claim 1, wherein the linear conductor and the elliptical ring conductor are shaped like a sheet having a width.

3. The magnetic resonance imaging apparatus according to claim 1, wherein the coil further comprises either of two feeding ports and four feeding ports for feeding RF (radiofrequency) signals to the coil, and wherein the feeding ports are arranged at positions line-symmetrical with respect to either one of the major axis and the minor axis of the elliptical ring like conductor, and as for two of the feeding ports being adjacent in a circumferential direction of the elliptical ring conductor, when power is fed to one feeding port, amplitude of RF current flowing in the other feeding port is minimized.

4. The magnetic resonance imaging apparatus according to claim 1, wherein the coil further comprises a shield outside the elliptical ring conductor, the plurality of linear conductors being covered with the shield.

5. The magnetic resonance imaging apparatus according to claim 4, wherein a distance between the elliptical ring like conductor and the shield is constant with respect to the circumferential direction of the elliptical ring like conductor.

6. The magnetic resonance imaging apparatus according to claim 4, wherein a distance between the elliptical ring conductor and the shield becomes shorter along with going away from the minor axis toward the major axis of the elliptical ring conductor.

7. The magnetic resonance imaging apparatus according to claim 1, further comprising:

a magnetic decoupling circuit for preventing mutual magnetic coupling, wherein the magnetic decoupling circuit is arranged on either of the linear conductor or the elliptical ring conductor.

8. The magnetic resonance imaging apparatus according to claim 7, wherein the magnetic decoupling circuit is a PIN diode.

9. The magnetic resonance imaging apparatus according to claim 7, wherein the magnetic decoupling circuit comprises a circuit where the PIN diode and an inductor are connected in series, and a capacitor is connected in parallel with the circuit.

10. The magnetic resonance imaging apparatus according to claim 1, further comprising:

an RF (radiofrequency) magnetic field signal generator which generates an RF magnetic field signal; and a signal processor which subjects a detection signal to a signal processing, wherein the coil irradiates a test subject with the RF magnetic field signal inputted from the RF magnetic field signal generator, detects a magnetic resonance signal issued from the test subject, and outputs the magnetic resonance signal as the detection signal to the signal processor.

11. The magnetic resonance imaging apparatus according to claim 7, further comprising:

an RF (radiofrequency) magnetic field signal generator which generates an RF magnetic field signal and a reception coil which detect a magnetic resonance signal issued from a test subject, and outputting the signal as a detection signal, wherein the coil irradiates the test subject with the RF magnetic field signal inputted from the RF magnetic field signal generator.

12. A magnetic resonance imaging apparatus comprising:

a coil, the coil comprising:

two elliptical ring conductors having an arc at least partially, the two elliptical ring like conductors being arranged in parallel with each other;

a plurality of linear conductors, both ends of each of the plurality of linear conductors being connected to the elliptical ring conductors, respectively; and a plurality of capacitors, each of the plurality of capacitors comprising at least one capacitor and each of the plurality of capacitors having a substantially identical capacitance, wherein at least one of the plurality of capacitors is arranged one by one on a linear conductor and/or on an arc-shaped conductor, the arc-shaped conductor forming a part of the elliptical ring conductor, and the arc-shaped conductor being placed between connection points of the linear conductors which are adjacent, and wherein the plurality of linear conductors are arranged line symmetrically with respect to a major axis and a minor axis of the elliptical ring conductor, and wherein a width of each of the plurality of linear conductors increases along with going away from the minor axis toward the major axis of the elliptical ring conductor.

13. The magnetic resonance imaging apparatus according to claim 12, wherein each of the linear conductor and the elliptical ring conductor is shaped like a sheet having a width.

14. The magnetic resonance imaging apparatus according to claim 12, wherein the coil further comprises either of two feeding ports and four feeding ports for feeding RF (radiofrequency) signals to the coil, and wherein the feeding ports are arranged at the positions line-symmetrical with respect to either one of the major axis and the minor axis of the elliptical ring conductor, and as for two of the feeding ports, which are adjacent in a circumferential direction of the elliptical ring conductor, when power is fed to one of the two feeding ports, amplitude of RF current flowing in the other of the two feeding ports is minimized.

15. A magnetic resonance imaging apparatus comprising:

a coil, the coil comprising:

two elliptical ring conductors having an arc shape at least partially, the two elliptical ring conductors being arranged in parallel with each other;

a plurality of linear conductors, both ends of each of the plurality of linear conductors being connected to the elliptical ring conductors, respectively; and a plurality of capacitors, each of the plurality of capacitors comprising at least one capacitor and each of the plurality of capacitors having a substantially identical capacitance, wherein at least one of the capacitors is arranged one by one, on the linear conductor and/or on an arc-shaped conductor forming a part of the elliptical ring conductor, the arc-shaped conductor being placed between connection points of the linear conductors, which are adjacent, and wherein the plurality of linear conductors are arranged line symmetrically with respect to a major axis and a minor axis of the elliptical ring conductor, and wherein an electrical phase difference between two arc-shaped conductors, which are adjacent, increases along with going away from a minor axis toward a major axis of the elliptical ring conductor, and the electrical phase difference is 180 degrees between two of the arc-shaped conductors that are positioned point-symmetrically with respect to the center of the elliptical ring conductor.

16. The magnetic resonance imaging apparatus according to claim 15, wherein a distance between the centers of two of the adjacent linear conductors increases along with going away from the minor axis toward the major axis of the elliptical ring conductor.

17. The magnetic resonance imaging apparatus according to claim 15, wherein each of the linear conductor and the elliptical ring conductor is shaped like a sheet having a width, and wherein the width of the linear conductor increases along with going away from the minor axis toward the major axis of the elliptical ring conductor.

18. The magnetic resonance imaging apparatus according to claim 15, wherein the coil further comprises either of two feeding ports and four feeding ports for feeding RF (radiofrequency) signals to the coil, and wherein the feeding ports are arranged at positions line-symmetrical with respect to either one of the major axis and the minor axis of the elliptical ring conductor, and as for two of the feeding ports, which are adjacent in a circumferential direction of the elliptical ring conductor, when power is fed to one of the two feeding ports, amplitude of RF current flowing in the other of the two feeding ports is minimized.

* * * * *